(12) United States Patent  
Baba

(10) Patent No.: US 8,787,520 B2  
(45) Date of Patent: Jul. 22, 2014

(54) RADIATION IMAGING DEVICE

(75) Inventor: Rika Baba, Kodaira (JP)

(73) Assignee: Hitachi Medical Corporation, Tokyo (JP)

( * ) Notice: Subject to any disclaimer, the term of this patent is extended or adjusted under 35 U.S.C. 154(b) by 452 days.

(21) Appl. No.: 13/131,604

(22) PCT Filed: Nov. 24, 2009

(86) PCT No.: PCT/JP2009/069785  
§ 371 (c)(1),  
(2), (4) Date: May 26, 2011

(87) PCT Pub. No.: WO2010/061810  
PCT Pub. Date: Jun. 3, 2010

(65) Prior Publication Data  
US 2011/0235773 A1    Sep. 29, 2011

(30) Foreign Application Priority Data

Nov. 27, 2008   (JP) ................................. 2008-302703

(51) Int. Cl.  
*A61B 6/03* (2006.01)  
*G06T 11/00* (2006.01)

(52) U.S. Cl.  
CPC ................................... *G06T 11/005* (2013.01)  
USPC ............................................ 378/7; 382/131

(58) Field of Classification Search  
CPC .......... A61B 6/03; A61B 6/504; A61B 6/481; A61B 6/466; A61B 6/027; A61B 6/583; A61B 6/4441; A61B 6/482; A61B 6/5282; A61B 5/055; A61B 6/12; A61B 6/4291; A61B 6/469; A61B 6/505; A61B 6/585; A61B 6/06; A61B 6/4464; A61B 6/488; A61B 6/4035; A61B 6/405; A61B 6/4085; A61B 6/4233; A61B 6/4241; A61B 5/4244; A61B 6/035; A61B 6/483; A61B 6/5205; A61B 6/5258; A61B 6/542; A61B 6/563; A61B 6/032; G06T 11/005; G06T 2211/404; G06T 5/50; G06T 11/006; G06T 11/008; G06T 2207/20224; G06T 2211/421; G06T 2207/20128; G06T 2207/30008; G06T 2207/30052; G06T 2207/30101; G06T 5/10; G06T 7/0026; G06T 7/0083; G06T 7/0089; G01N 23/046; G01N 21/538; G01N 23/04; Y10S 378/901; Y10S 128/922; G01T 1/2985; G01T 1/1648; G01T 1/24; G01T 1/00; G01T 1/1647  
USPC ................................................ 378/7; 382/131  
See application file for complete search history.

(56) References Cited

U.S. PATENT DOCUMENTS 7,269,246 B2 *   9/2007   Ohishi ........................ 378/98.12

FOREIGN PATENT DOCUMENTS

| JP | 4-170942 | | 6/1992 |
| JP | 6-319730 | | 11/1994 |
| JP | 7-275236 | | 10/1995 |
| JP | 2002017714 A | * | 1/2002 |
| JP | 2006-239118 | | 9/2006 |
| JP | 2008-220653 | | 9/2008 |

OTHER PUBLICATIONS

Vedula et al., Beam Hardening Corrections in Quantitative Computed Tomography, 2007, AIP Conference Proceedings, vol. 894, pp. 546-552.*  
Love et al., Convolution filtering technique for estimating scatter distributions in radiographic images, 1986, SPIE, vol. 626, pp. 275-283.*  
Endo et al., Magnitude and effects of x-ray scatter in 256-slice CT scanner, 2006, Medical Physics, vol. 33, No. 9, pp. 3359-3368.*  
Baba et al., Scattered X-ray Correction Method for Cone-Beam CT, May 2009, vol. 27, No. 3, pp. 177-184.*  
Phoenix Translations, USPTO 13-6015, English translation of Baba et al., Scattered X-ray Correction Method for Cone-Beam CT, May 2009, vol. 27, No. 3, pp. 177-184.*

* cited by examiner

Primary Examiner — Toan Ton
Assistant Examiner — John Corbett
(74) Attorney, Agent, or Firm — Brundidge & Stanger, P.C.

(57) ABSTRACT

Disclosed is an X-ray imaging apparatus in which a correction function used to correct scattered X-rays and a correction function used to correct beam hardening can be simply and precisely determined so that the correcting operations are performed in an appropriate sequence using the correction functions thus determined to enhance the precision in the correction and improve the image quality. The scattered X-rays and the beam hardening are corrected sequentially in this order, using the scattered X-ray correction function and the beam hardening correction function, both calculated using measured data for calculating the correction functions. The scattered X-ray correction function approximates as to each transmission distance, the data measured with changes in the transmission distance and with changes in the scattered X-ray amount, and associates the correction value thus obtained with transmittance data. Upon calculation of the beam hardening correction function, data measured with changes in the transmission distance is converted into projection data and is linearly approximated to obtain an ideal amount of beam hardening.

20 Claims, 17 Drawing Sheets

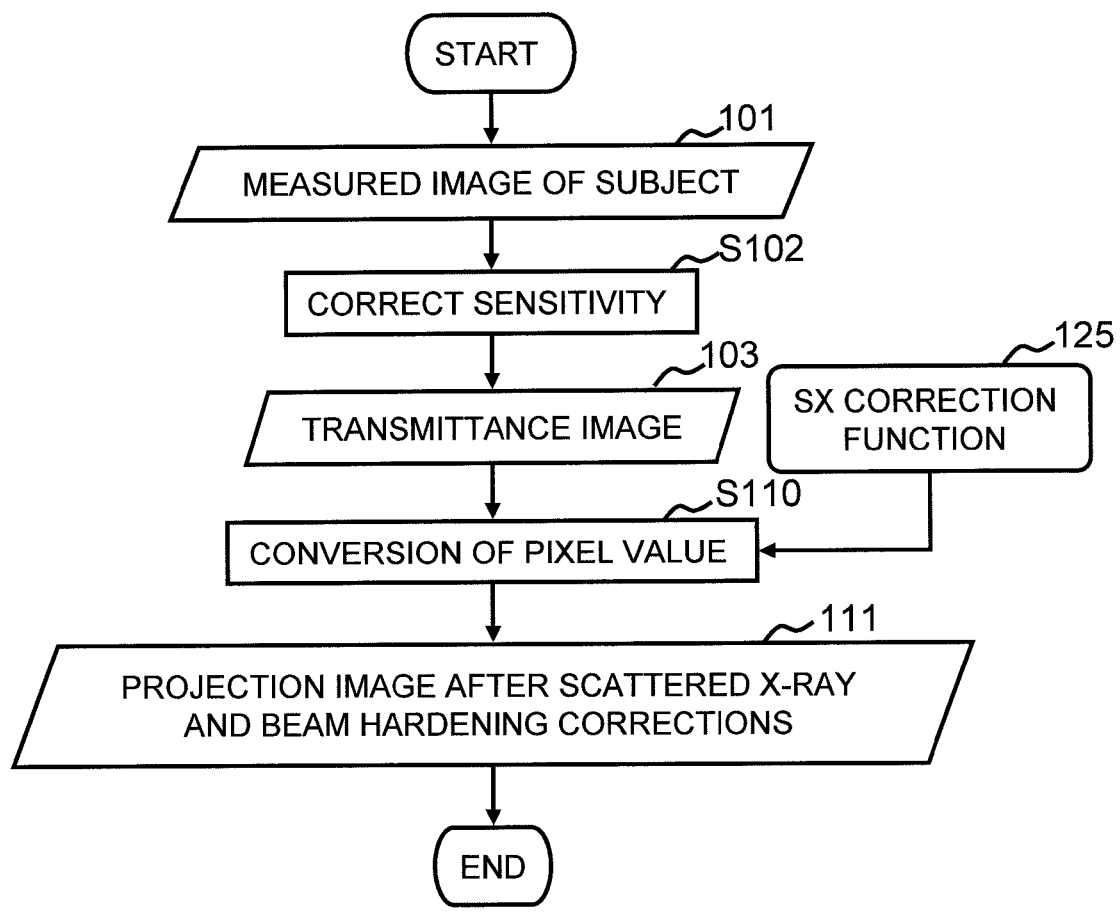

RADIATION IMAGING DEVICE

TECHNICAL FIELD

The present invention relates to a technique to enhance image quality in a radiation imaging apparatus. More particularly, the present invention relates to a technique for effectively correcting influences of scattered radiation and beam hardening.

BACKGROUND ART

A radiation imaging apparatus measures radiation (X-rays) passing through a subject, and obtains a static image or a moving image of the subject. On this occasion, scattered X-rays and beam hardening are considered as factors which reduce image contrast and precision of measured values and deteriorate image quality. The scattered X-rays, which are generated when X-rays pass through the subject, are mixed with direct X-rays being a net transmission amount, and incident on a detector which detects X-rays. The beam hardening, which occurs when X-rays passes through the subject and a part of energy is absorbed by the subject, causing variations in energy distribution, changes an X-ray absorption coefficient of the subject.

By way of example, there is known a technique for correcting influences of scattered X-rays and beam hardening on measured data in a cone beam CT (e.g., see the patent document 1).

PRIOR ART REFERENCES

Patent Document

Patent Document 1: Japanese Unexamined Patent Application Publication No. 2006-239118

SUMMARY OF THE INVENTION

Problem to be Solved by the Invention

In order to perform highly precise correction on influences of scattered X-rays and beam hardening, it is necessary to favorably separate those influences and obtain highly precise correcting functions respectively. The patent document 1 describes to separate those influences for correction, but it refers to none of the followings; a specific separation method, a correction method, and the functions used for the correction.

In addition, the patent document 1 describes to perform the correction on the scattered X-rays (hereinafter, referred to as "scattered X-ray correction") after the correction on the beam hardening is performed (hereinafter, referred to as "beam hardening correction"). An effect that the beam hardening has on the measured data varies sensitively depending on the thickness of the subject. On the other hand, an effect that the scattered X-rays have on the measured data is slow to respond to a local change of the subject. Therefore, if the corrections are performed sequentially in the order as described above, local variation of the subject have too much influences on the scattered X-ray correction, and this may cause an excessive correction.

The present invention has been made in view of the situation above, and the object of the invention is to provide a technique of an X-ray imaging apparatus which determines a correcting function for correcting scattered X-rays and a correcting function for correcting beam hardening, easily with high precision, and performs corrections in an appropriate order by using thus determined correction functions with a high degree of correcting precision, thereby improving the precision in correction and enhancing an image quality.

Means to Solve the Problem

In the present invention, by using a beam hardening correction function and a scattered X-ray correction function which are calculated from measured data for calculating the correction functions, the scattered X-ray correction and the beam hardening correction are performed sequentially in this order. The scattered X-ray function approximates data items as to each transmission distance, the data items being measured with changes in a transmission distance and with changes in a scattered X-ray amount, and associates a correction value being obtained with transmittance data. On the other hand, the beam hardening correction function converts data items measured with changes in the transmission distance into projection data items, and obtains an ideal value as a beam hardening amount by subjecting the projection data items to linear approximation.

Specifically, the present invention is directed to providing radiation imaging apparatus, comprising, a radiation source for irradiating a subject with radiation, a detector having multiple pixels for detecting the radiation, a storage means for storing a scattered radiation correction function for correcting influence of scattered radiation on a detection result obtained from the detector, and a beam hardening correction function for correcting influence of beam hardening on the corrected detection result, and a correction means for correcting the detection result by the scattered radiation correction function, and for correcting the corrected detection result by the beam hardening correction function.

The present invention may be directed to providing the radiation imaging apparatus, wherein, the beam hardening correction function is a linear function passing through an original point, obtained by approximating a relation between a first projection data item obtained by converting the detection result measured with changes in the transmission distance when the scattered radiation amount is set to be nearly zero, and a second projection data item calculated from a function that returns the beam hardening amount in accordance with the transmission distance, and further the beam hardening correction function returns a beam hardening correction value in response to the corrected detection result after correcting the influence of the scattered radiation; and the correction means corrects transmittance data obtained from the detection result from the detector using the scattered radiation correction function, then converts the corrected transmittance data into a third projection data item, and replaces the third projection data item by the beam hardening correction value associated with the third projection data item, thereby correcting the influence of the beam hardening.

The present invention may be directed to providing the radiation imaging apparatus, wherein, the scattered radiation correction function is obtained by approximating a relation between a first transmittance data item corresponding to a first scattered radiation amount obtained from a first function that approximates a relation between the transmittance data and the scattered radiation amount with respect to each transmission distance, and a difference value obtained by subtracting the transmittance data when the scattered radiation amount obtained from the first function is nearly zero from the first transmittance data item, and further the scattered radiation correction function is a function for returning a correction value of the scattered radiation amount in response to the detection result; and the correction means converts the detection result detected by the detector using the first scattered radiation amount, into the transmittance data, and corrects the influence of the scattered radiation by subtracting the correction value calculated from the transmittance data, from the transmittance data.

Alternatively, the present invention may be directed to providing a radiation imaging apparatus, wherein, the scattered radiation correction function is obtained by approximating a relation between a first transmittance data item corresponding to a first scattered radiation amount obtained from a first function that approximates a relation between the transmittance data and the scattered radiation amount with respect to each transmission distance, and a second transmittance data when the scattered radiation amount obtained from the first function is nearly zero, and further the scattered radiation correction function is the function for returning a correction value of the scattered radiation amount according to the detection result, and the correction means converts the first detection result detected by the detector using the first scattered radiation amount, into the transmittance data, and corrects the influence of the scattered radiation by replacing the transmittance data with the correction value calculated from the transmittance data.

Effect of the Invention

According to the present invention, it is possible to use in the X-ray imaging apparatus, a correction function for the scattered X-ray correction and a correction function for the beam hardening correction, the functions being easily generated and having a high degree of correction precision, and to perform corrections sequentially in appropriate order. Therefore, precision in correction is enhanced, thereby improving the image quality.

BRIEF DESCRIPTION OF DRAWINGS

FIG. 17 is a flow of the correction process according to the fifth embodiment.

MODES FOR CARRYING OUT THE INVENTION

<<First Embodiment>>

Hereinafter, the first embodiment to which the present invention is applied will be explained. In all the drawings for explaining each of the embodiments of the present invention, the constituents having the same function are labeled the same, and tedious explanations shall not be made.

Figure 1:
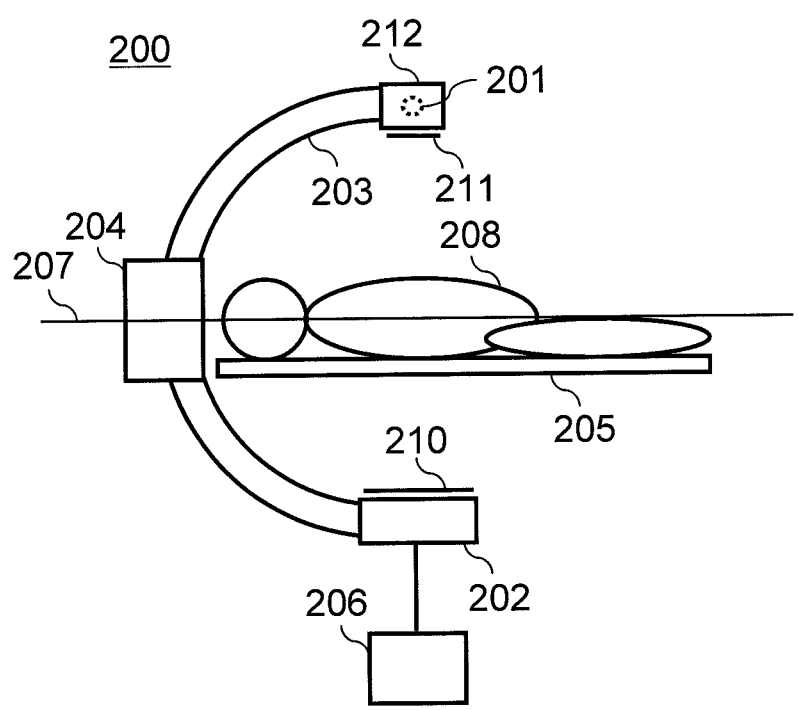
FIG. 1 is a side view of the X-ray imaging apparatus according to the first embodiment.

FIG. 1 is a side view of the X-ray imaging apparatus 200 according to the present embodiment. The X-ray imaging apparatus 200 according to the present embodiment is provided with an X-ray source 201 within an X-ray tube 212, a detector 202, a support 203, a rotation device 204, a subject holder 205, and a control processor 206. The X-ray source 201 and the detector 202 are placed in opposed manner respectively on both ends of the support 203. Here, a C-shaped arm is employed as the support 203, and a bed is employed as the subject holder 205. The rotation device 204 allows the support 203 to rotate around the subject holder 205. Along with the rotation of the support 203, the X-ray source 201 and the detector 202 rotates around a subject 208 on the subject holder 205, using a rotation axis 207 as the center. In this figure, the rotation axis 207 is assumed as parallel with the floor, and the X-ray source 201 and the detector 202 installed on the support 203 rotate around the subject 208 who lies on the bed.

Figure 2:
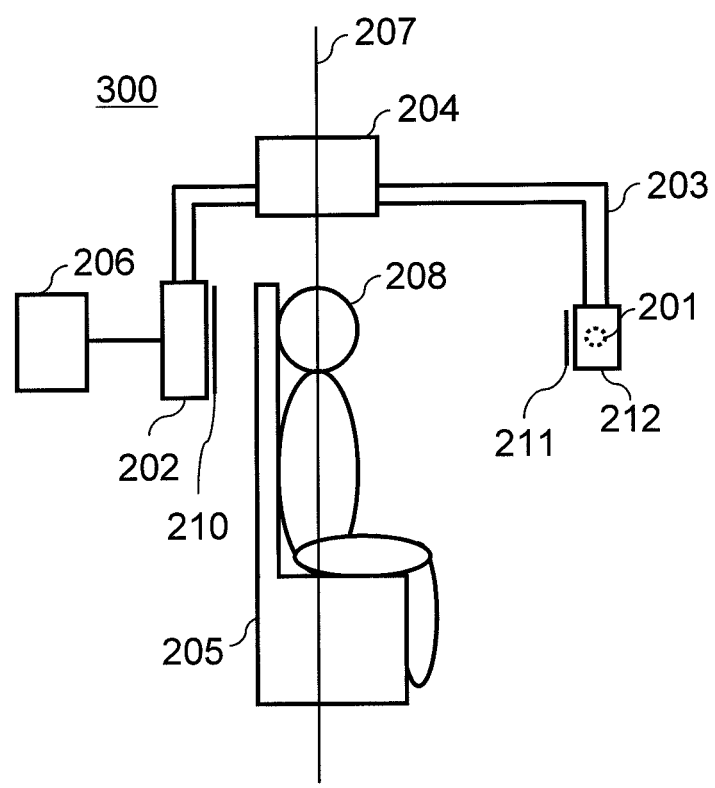
FIG. 2 is a side view of another X-ray imaging apparatus according to the first embodiment.

It is to be noted that the X-ray imaging apparatus 200 of the present embodiment is not limited to the example described above. FIG. 2 shows an example of another X-ray imaging apparatus 300 according to the present embodiment. In this figure, the constituents having the same functions as those of the X-ray imaging apparatus 200 of FIG. 1 are labeled the same. The X-ray imaging apparatus 300 is provided with basically the same configuration as the X-ray imaging apparatus 200. However, a U-shaped arm is employed as the support 203 which is suspended from another support fixed on the floor. A chair is employed as the subject holder 205. The rotation axis 207 is perpendicular to the floor and the X-ray source 201 and the detector 202 rotates around the subject 208 sitting on the chair, within a plane in parallel with the floor surface.

Figure 3:
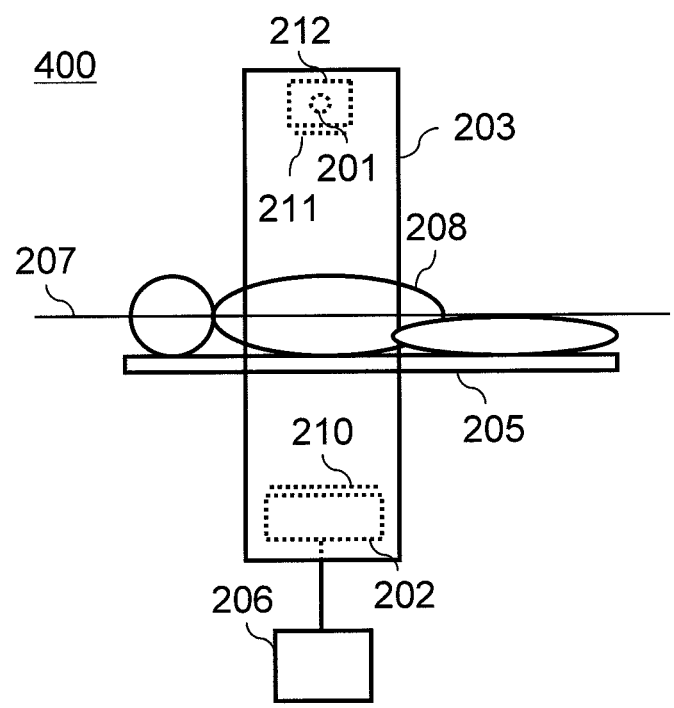
FIG. 3 is a side view of another X-ray imaging apparatus according to the first embodiment.

FIG. 3 shows an example of another X-ray imaging apparatus 400 according to the present embodiment. In this figure, the constituents having the same functions as those of the X-ray imaging apparatus 200 of FIG. 1 are labeled the same. The X-ray imaging apparatus 400 is provided with basically the same configuration as the X-ray imaging apparatus 200. However, a gantry is employed as the support 203 and it rotates by the rotation device 204 not illustrated.

It is to be noted that, alternatively, a lateral U-shaped arm or the like may be employed as the support 203. Another configuration such as suspending the support 203 from the ceiling or the support 203 is held on the floor may be applicable.

Further in these X-ray imaging apparatuses 200, 300, and 400, either one or both of the support 203 and the subject holder 205 are moved, and the rotation axis 207 may be set obliquely with respect to the body axis of the subject 208. It is further possible to fix the X-ray source 201 and the detector 202, and rotate the subject 208 that is placed on a turntable or the like. Alternatively, both the X-ray source 201 and the detector 202, and the subject 208 may be rotated together.

Referring to FIG. 1 again, in the X-ray imaging apparatus 200 of the present embodiment, the X-rays irradiated from the X-source 201 pass through the subject 208, the detector converts the X-rays into electrical signals in accordance with X-ray intensity, and those signals are inputted in the control processor 206 in the form of a measured image. It is possible to install a grid 210 between the detector 202 and the subject 208 for shielding against the scattered X-rays. It is further possible to install a collimator 211 between the X-ray source 201 and the subject 208 for adjusting the range of X-rays to be irradiated on the subject 208.

It is to be noted that in the present embodiment, a two-dimensional detector is employed as the detector 202. One-dimensional detectors placed in multiple rows may also be assumed as the two-dimensional detector. The two-dimensional detector may be a flat-type X-ray detector, a combination of an X-ray image intensifier and a CCD camera, an imaging plate, a CCD detector, a solid state detector, or the like. The flat-type X-ray detector may be formed in such a manner that a pair of amorphous silicon photo diode and TFT is placed on a square matrix, and then they are directly combined with a fluorescent screen.

The control processor 206 is an information processor provided with a CPU and a memory, and realizes a measurement control section for performing measurement to obtain a measured image by controlling operations of each section of the X-ray imaging apparatus 200, and a correction processing section for executing a correction process on the measured image to obtain a corrected image. By way of example, the measurement control section controls generation of X-rays from the X-ray source 201, acquisition of data by the detector 202, and rotation of the support 203 by the rotation device 204, thereby realizing rotation measurement which performs X-ray irradiation and acquisition of the measured image while the support 203 is rotated. The control processor 206 may perform reconstruction processing on the corrected image to acquire a three-dimensionally reconstructed image.

The control processor 206 is provided with a storage device (not illustrated) and an input device (not illustrated). The input device may be a keyboard, a pointing device such as a mouse, or the like. The storage device stores the correction function used for the correction process, a parameter used for the correction process, a type of correction mode, and the like. It is further possible to configure such that the X-ray imaging apparatus 200, itself, generates the correction function. For this case, the control processor 206 is provided with a correction function generating section. The storage device further stores a type of implementation mode in the process for generating the correction function (correction function generation process), a parameter used in the correction function generation process, and the like. These are held by the storage device according to a means such as reading from a file via the input device or replacement of storage chips. The storage device further holds descriptions of an instruction inputted from the user via the input device. The descriptions may indicate, for example, whether or not the correction process is to be implemented, a correction mode being selected, whether or not the correction function generating process is performed during calibration or maintenance, and the like.

The implementation mode of the correction function generation process indicates the timing for the correction function generating section to conduct measurement for generating the correction function (measurement for generating correction function) and specify the timing for generating the correction function. By way of example, some mode types are prepared for performing the correction function generation process, respectively, at "the time when the apparatus is installed", "the time of maintenance", "the time of calibration", "the time when a user desires", and the like. The correction mode indicates the timing for the correction processing section to perform correction. By way of example, the mode types include, "real time mode" for performing correction process on real time when fluoroscopy and measurement are performed, "on-line mode" for performing correction in a preprocessing of the reconstruction operation, "off-line mode" for performing the correction process, independently of the measurement and the image reconstruction process, and the like. If the correction function is stored in the storage device in advance, it is not necessary to provide the correction function generation section, the implementation, mode of the correction function generation measurement, parameters, or the like.

In the present embodiment, data directly obtained by measuring the subject 208 is referred to as measured data. Data obtained by dividing the measured data by sensitivity data of the detector 202, is referred to as transmittance data. The transmittance data is data that is obtained by excluding from the measured data, unevenness due to a device such as sensitivity of the detector 202. The sensitivity data can be obtained by performing measurement without placing the subject 208. Furthermore, the transmittance data is subjected to logarithmic conversion and then multiplied by (−1), so as to obtain data referred to as projection data. In addition, the "data" indicates a measured result as to one pixel or a partial region on an image, and an aggregate of data is referred to as an image (measured image, transmittance image, and projection image).

Next, the correction process will be explained, which is performed by the correction processing section in the X-ray imaging apparatus 200 according to the present embodiment. The correction processing section according to the present embodiment uses the correction function held in the storage device, corrects the measured data, and obtains projection data after the correction is performed. In the present embodiment, there are provided as the correction function, a beam hardening correction function for correcting the influence of beam hardening (hereinafter, referred to as "BH correction function"), and a scattered X-ray correction function for correcting the influence of the scattered X-rays (referred to as "SX correction function").

Figure 4:
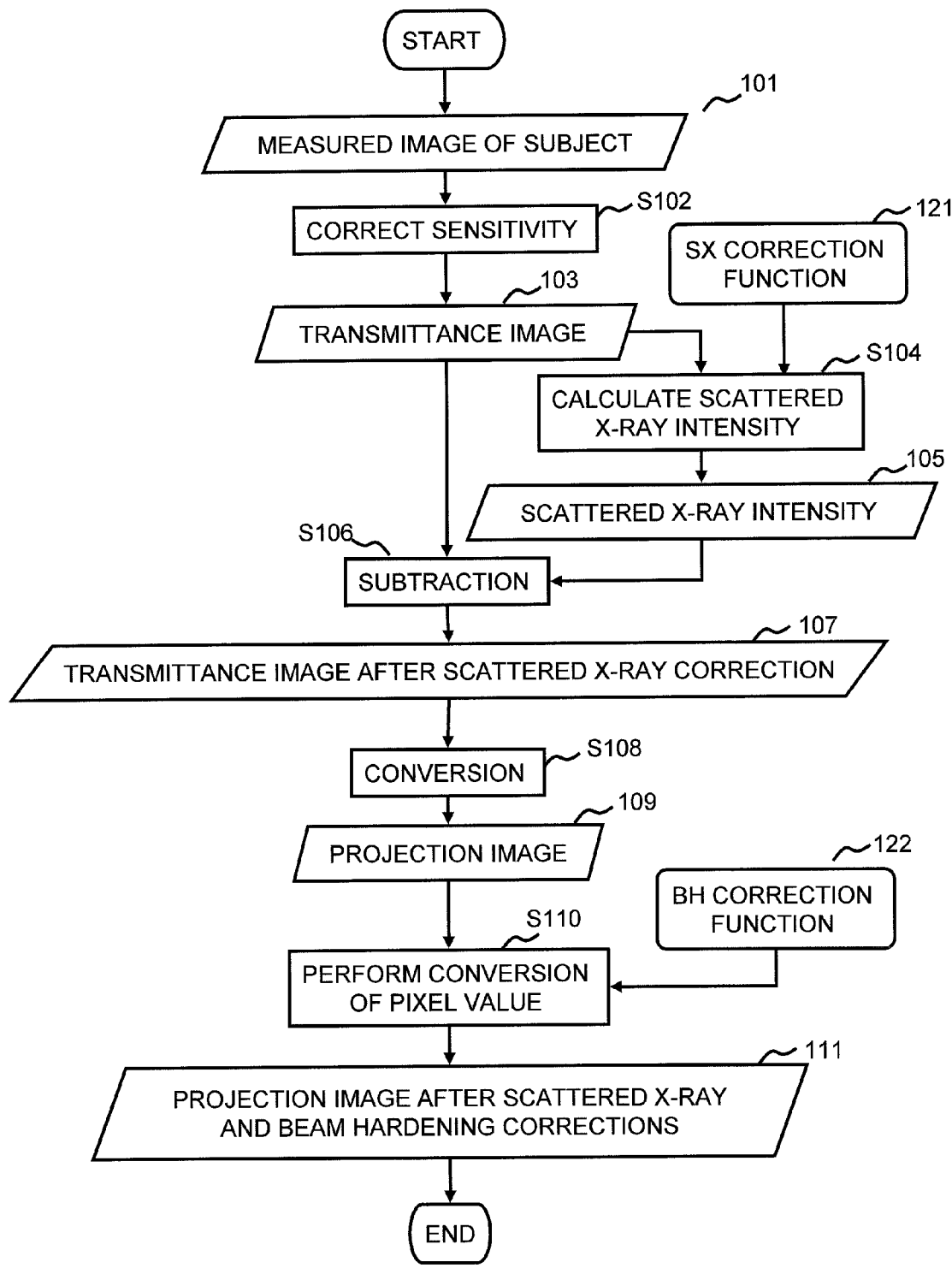
FIG. 4 is a flow of a correction process according to the first embodiment.

FIG. 4 is a processing flow of the correction process performed by the correction processing section according to the present embodiment. Firstly, measured data (measured image) 101, corresponding to one image that is obtained when the measurement control section takes an image of the subject using a desired scattered X-ray amount, is subjected to sensitivity correction (S102), and transmittance data (transmittance image) 103 corresponding to one image is obtained.

Next, the scattered X-ray correction on the transmittance data 103 is performed using the SX correction function 121 so as to obtain transmittance data after the scattered X-ray correction (transmittance image after scattered X-ray correction) 107. Specifically, scattered X-ray intensity 105 associated with each transmittance data 103 is calculated (step S104). Then, the scattered X-ray intensity 105 being obtained is subtracted from each transmittance data 103 (step S106), and the transmittance data after the scattered X-ray correction (transmittance image after scattered X-ray correction) 107 is obtained, in which the influence of scattered X-rays corresponding to one image has been corrected.

Next, each transmittance data 107 after the scattered X-ray correction is subjected to logarithmic conversion and multiplied by (−1) (step S108), thereby obtaining the projection data (projection image) 109 corresponding to one image. The projection data 109 corresponding to one image being obtained is subjected to the beam hardening correction by using the BH correction function 122 (step S110). Then, the projection data after the beam hardening correction corresponding to one image (projection image after the scattered X-ray correction and the beam hardening correction) 111 is obtained. It is to be noted that in the correction processes described above, each data (image) generated by the correction processing section is stored in the storage device.

Next, there will be explained details of the correction function generation process for generating the SX correction function 121 and the BH correction function 122 which are used in the correction processes described above. These correction functions are obtained from data measured in advance by using a simulated subject. The correction function generation process is carried out at a timing that is designated as the aforementioned implementation mode of the correction function generation process. By way of example, this process may be carried out as a preliminary measurement immediately before real measurement, or it may be carried out independently of the real measurement, such as executed at the time of installing the X-ray imaging apparatus 200. The correction function generation process is implemented when the CPU executes an operation process according to a program in the information processor. It is possible to configure such that the controller 206 also serves as the information processor. Alternatively, the information processor may be provided independently of the X-ray imaging apparatus 200, and only the SX correction function and the BH correction function being obtained are stored in the storage device of the X-ray imaging apparatus 200 of the present embodiment. Hereinafter, in the present embodiment, there will be explained the case where the correction function generation processing section of the X-ray imaging apparatus 200 generates the correction functions.

Firstly, there will be explained an overview of the BH correction function generation process for generating the BH correction function 122 in the correction function generation process. When it is assumed that the thickness of the subject is t and the absorption coefficient is µ, the beam hardening amount is represented by µt in the projection data. In the present embodiment, the beam hardening correction is performed on the projection data that is obtained from the transmittance data after the influence of the scattered X-rays is corrected. Therefore, in the present embodiment, in the state where the influence of the scattered X-rays is almost eliminated, multiple projection data items obtained by changing the thickness (transmission distance) t of the simulated subject are subjected to linear approximation, thereby determining a gradient corresponding to µ as mentioned above, and accordingly, determining the BH correction function which shows the correction amount of the projection data. Specific processing procedures are as the following.

Figure 5:
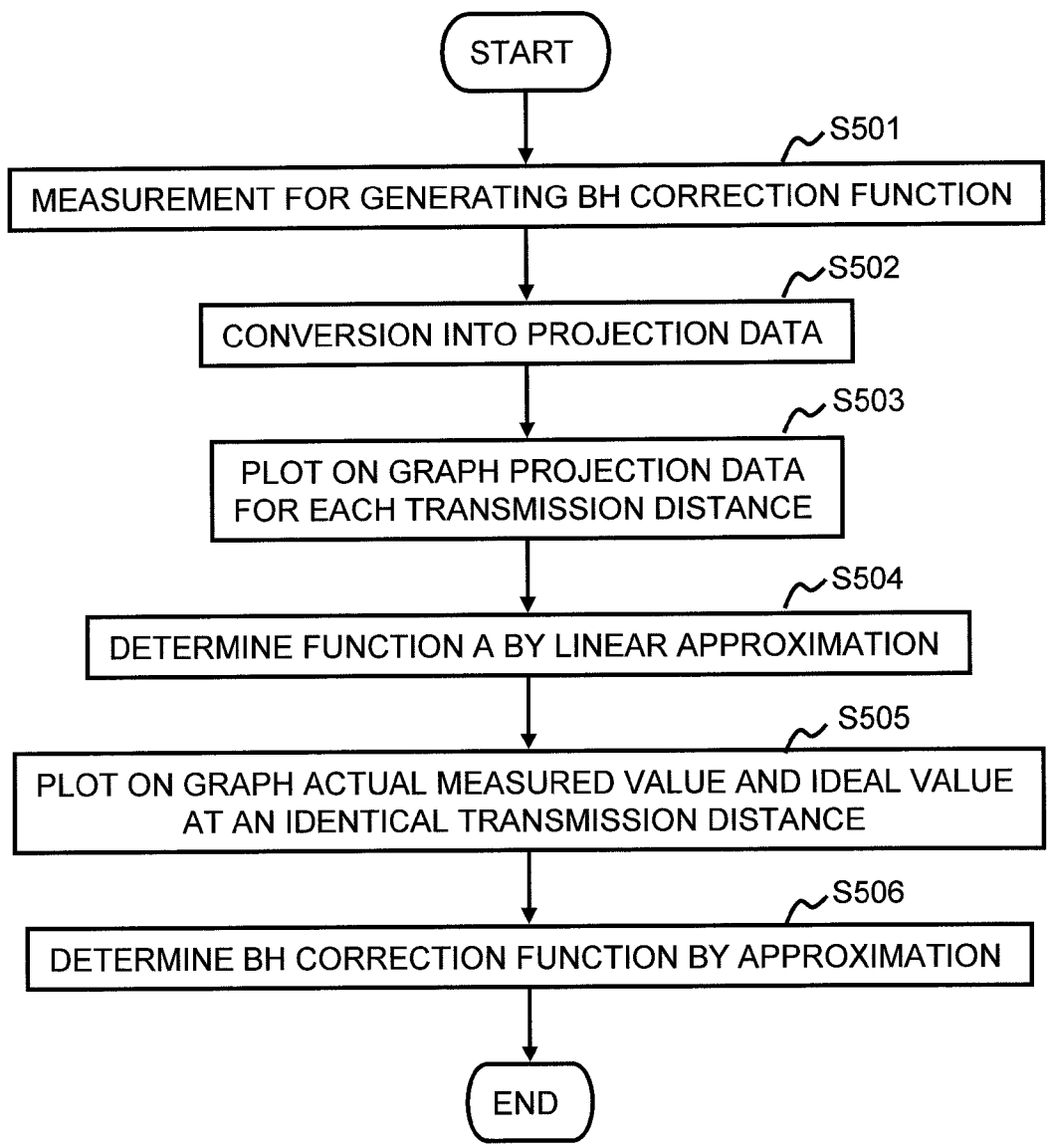
FIG. 5 is a flow of a process for generating the beam hardening correction function according to the first embodiment.

FIG. 5 is a process flow of the BH correction function generation process according to the correction function generation processing section. Under the condition that most of the influence of the scattered X-rays is eliminated to obtain only nearly direct X-rays, the measurement for generating the BH correction function (BH correction function generation measurement) is carried out (step S501) using simulated subjects having various thicknesses, thereby obtaining measured data (measured images) of the simulated subjects. Hereinafter, the scattered X-ray amount where the scattered amount is made as small as possible and includes only nearly direct X-rays is referred to as a specific scattered X-ray amount. In addition, a circular cylinder or a plate made of acryl, water, bone, or the like, may be employed as the simulated subject.

Transmittance data is obtained from the measured data being acquired, and the transmittance data is converted to obtain projection data (step S502). The projection data for each transmission distance is plotted on a graph (step S503). According to the graph, approximation is performed by the line passing through the origin in the region where the simulated subject is thin (the transmission distance is short), thereby determining the beam hardening amount calculation function (function A) in accordance with the transmission distance (step S504). Next, as to the same transmission distance, the projection data (real measured data) obtained in the step S502 are made to associate with the projection data (ideal value) calculated from the function A, plotted on the graph (step S505), approximated by a curved line passing through the origin, and the curved line is assumed as the BH correction function (step S506).

Next, there will be explained an overview of the SX correction function generation process for generating the SX correction function 121. Here, the function, in which the scattered X-ray intensity calculated from the transmittance data that is measured using the specific scattered X-ray amount is associated with the transmittance data corresponding to a scattered X-ray amount that is the same as the amount of real measurement, defines as the SX correction function.

Figure 6:
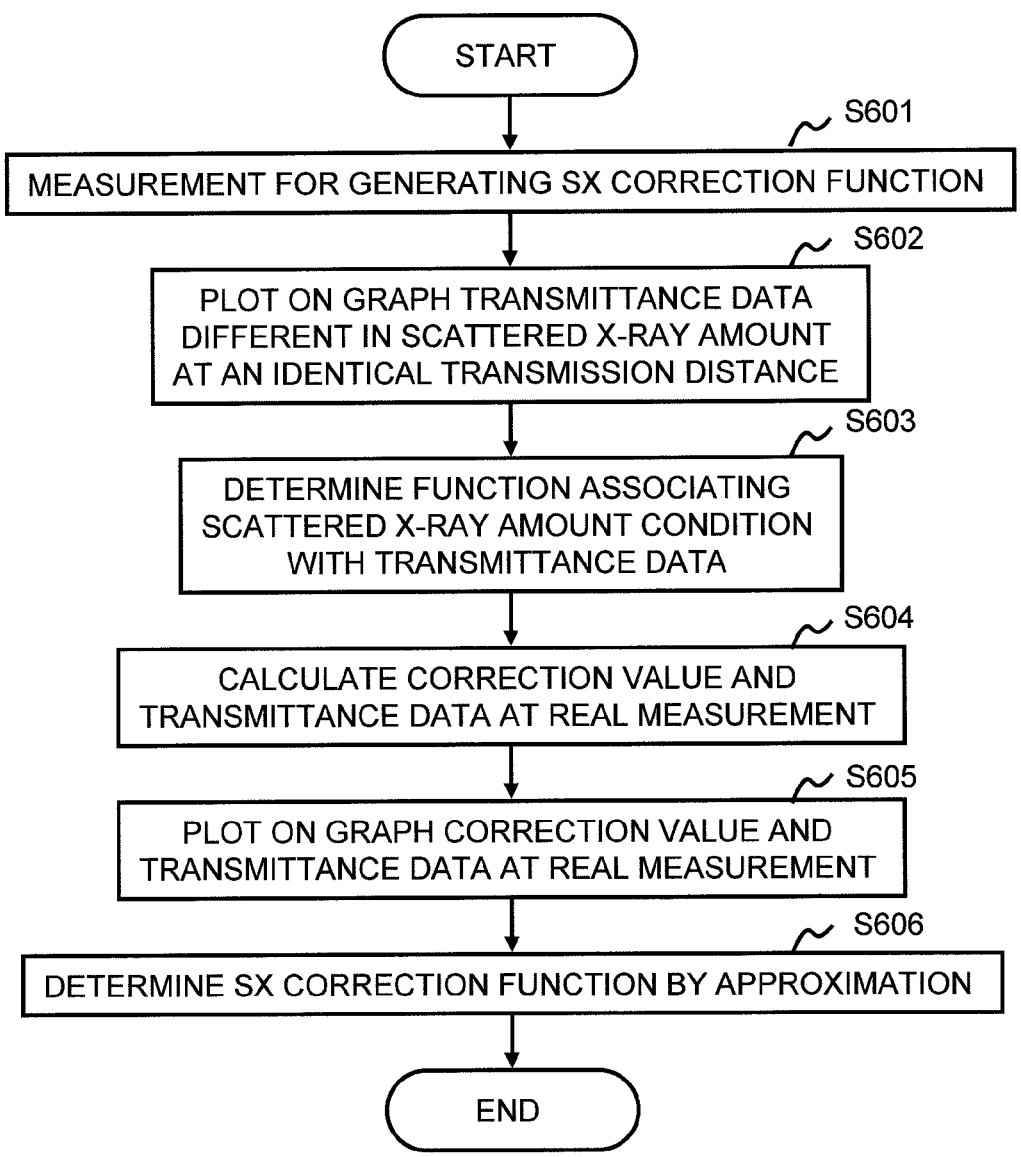
FIG. 6 is a flow of a process for generating the scattered X-ray correction function according to the first embodiment.

FIG. 6 is a process flow of the SX correction function generation process performed by the correction function generation processing section. Firstly, the SX correction function generation measurement is performed with the use of the simulated subject (step S601). In the SX correction function generation measurement, multiple measured data items are obtained by changing the scattered X-ray amount while keeping the transmission distance in the simulated subject constant. Transmittance data items are obtained from the measured data being acquired (measured data at the same transmission distance using different scattered X-ray amounts), and these transmittance data items are plotted on a graph (step S602). According to the plotted result, a function that relates a condition of the scattered X-ray amount with the transmittance data is determined (step S603). According to the function being determined, there are calculated a correction value using the specific scattered X-ray amount, and transmittance data under the same condition as the scattered X-ray amount when the real measurement (real measurement time transmittance data) is performed (step S604). It is to be noted that the correction value is obtained by subtracting from the real measurement-time transmittance data, the transmittance data under the specific scattered X-ray amount condition. With respect to various multiple transmission distances, the processes from the step S601 to the step S604 are repeated, and the correction values and the real measurement-time transmittance data are calculated respectively. Combinations of the obtained multiple correction values and the real measurement-time transmittance data items are plotted on a graph (step S605), and the SX correction function of the present embodiment is determined, which is the function associating the correction value with the real measurement-time transmittance data (step S606).

Figure 7:
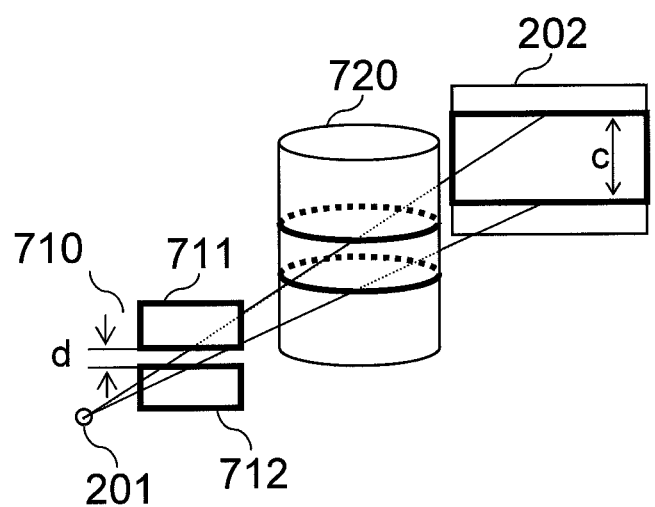
FIG. 7 is an illustration for explaining a method for changing a scattered X-ray amount in a measurement system according to the first embodiment.

Next, an explanation will be made as to details of each processing. Firstly, there will be explained a method for changing the scattered X-ray amount in a measurement system that is used in the correction function generation measurement. In the present embodiment, a collimator 211 is used to change the scattered X-ray amount. FIG. 7 is an illustration for explaining a method for changing the scattered X-ray amount in the measurement system according to the present embodiment. In the present embodiment, the collimator 710 (211) made up of two sheets of upper and lower shielding plates is used so that the scattered X-ray amount varies by changing the distance between the two sheets of the shielding plates. As shown in the figure, the X-rays, with a region of X-ray irradiation from the X-ray source 201 being restricted by the collimator 710, pass through the simulated subject 720 and they are incident on the detector 202. The distance d between the two sheets of shielding plates 711 and 712, which constitute the collimator 710, becomes width c on the measured image. The width c is increased and decreased in accordance with the increase and decrease of the distance d. Generally, the narrower the distance d between the two shielding plates becomes, the more the scattered X-ray amount is reduced, and a ratio of direct X-rays is increased. In other words, the width c is assumed as a condition to specify the scattered X-ray amount. Hereinafter, in the present embodiment, the width c on the measured image is referred to as collimator width c. It is further possible to configure such that the collimator condition may be indicated by an area, in the case where the collimator is made up of multiple shielding plates, or the collimator has a polygonal shape, a circular shape, an unspecified shape, or the like.

In addition, the transmission distance may be changed by using water cylinders having various diameters as the simulated subject 720, for instance. However, a method for changing the transmission distance is not limited to the way above. For example, it is possible to configure such that a detected position is changed on one water cylinder as the simulated subject, thereby acquiring transmittance data items which substantially have different transmission distances in the simulated subject 720. With the configuration as thus described, only one-time measurement allows acquisition of multiple transmittance data items having various transmission distances.

It is to be noted that the simulated subject 720 for acquiring different transmittance data items by varying the transmission distance is not limited to the water cylinder. By way of example, a phantom simulating a human body or an acrylic board having various thicknesses may be employed. Use of the phantom simulating the human body enables a correction with a high degree of precision, since it is close to the shape of an actual subject. It is further possible to use transmittance data of human body. This case enables a correction with much more high precision. Alternatively, transmittance data of an actual subject measured by the real measurement may be usable. In that case, a correction with the highest degree of precision may be performed. Also, it is possible to use simulated subjects having the same transmission distance but made of different materials, in order to acquire different transmittance data.

Next, a specific explanation will be made as to a procedure for generating the BH correction function 122 and the SX correction function 121 according to the result of the measurement for generating each of the correction functions. Firstly, a procedure for generating the BH correction function will be explained. In here, the measurement system as shown in FIG. 7, using m water cylinders each having a different diameter $x_j$ (j is a natural number between or equal to 1 and m, and m is a natural number) as the simulated subject, performs the BH correction function generation measurement setting the scattered X-ray amount to the specific scattered X-ray amount (step S501 in FIG. 5).

Here, the specific scattered X-ray amount is realized by setting the collimator width c to the width $c_0$ which is made as narrow as possible. It is because, the narrower the collimator width c is, the more influence of the scattered X-rays can be eliminated as described above. The measured data being obtained is converted into transmittance data, and further converted into projection data. Specifically, the projection data is calculated at the center position of the projection image that is obtained from the transmittance image. Hereinafter, the transmittance data and projection data obtained from the measured data which are measured with the collimator width c and the transmission distance x is represented as T (c, x) and P (c, x), respectively.

Figure 8:
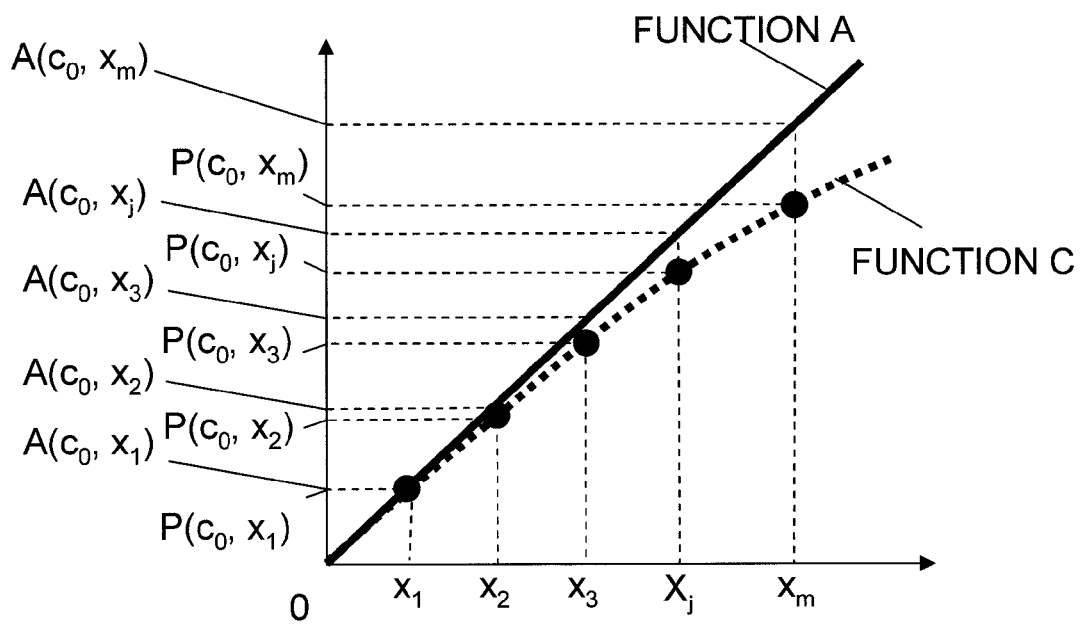
FIG. 8 is an illustration for explaining a method for deciding a beam hardening amount calculation function according to the first embodiment.

Each of the projection data items P ($c_0$, $x_j$) (1≤j≤m) being obtained are plotted on a graph, showing the transmission distance (a diameter of water cylinder used as the simulated subject) on the horizontal axis and showing the projection data P ($c_0$, $x_j$) on the vertical axis. FIG. 8 is a graph showing a result of the plotting. A straight line is specified, passing through the origin and fitting the plotted result within a region where a value of the diameter $x_j$ is small, and this line is assumed as an approximate expression representing function A ($c_0$, x) using the transmission distance x as a variable.

Figure 9:
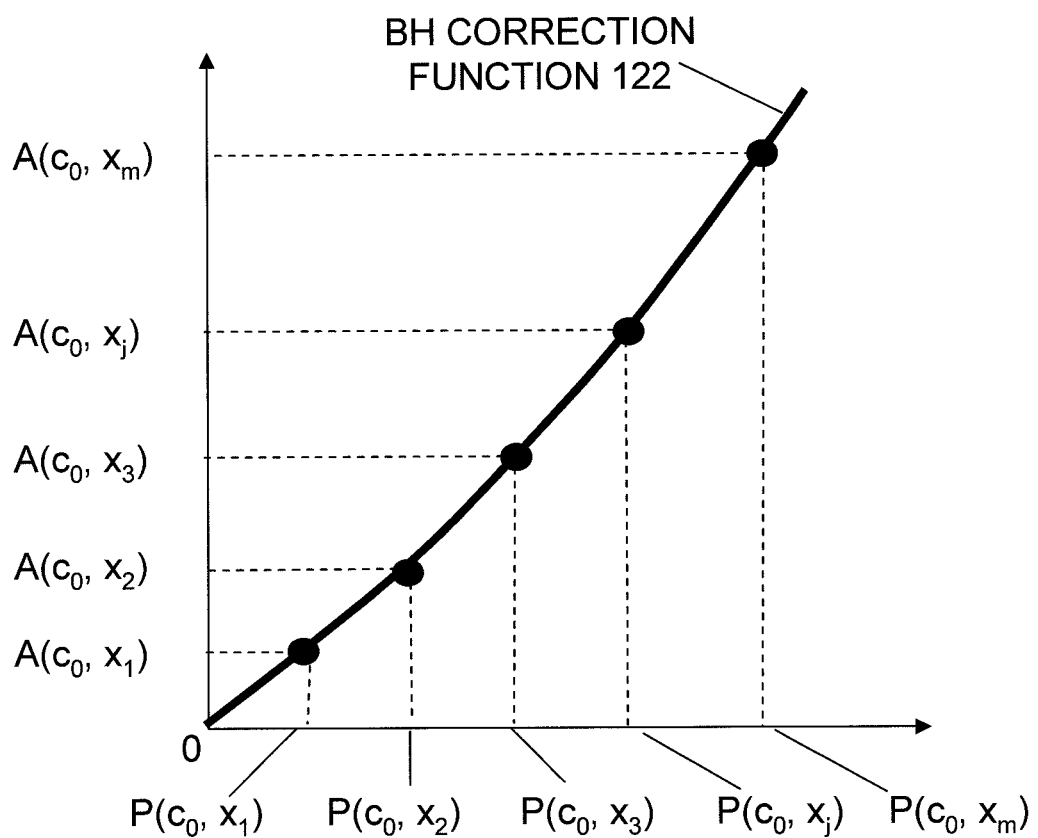
FIG. 9 is an illustration for explaining a method for deciding the beam hardening correction function according to the first embodiment.

As thus described, as to each transmission distance $x_j$, a combination of the projection data P ($c_0$, $x_j$) obtained from actual measured data and an ideal value A ($c_0$, $x_j$) obtained from the approximate expression is obtained. This combination is plotted on the graph showing the projection data P on the horizontal axis and showing the ideal value A on the vertical axis. FIG. 9 is a graph showing the result of the plotting. Then, an approximate curve passing through the origin and fitting the plotted result is determined, and it is assumed as the BH correction function 122. As thus described, the BH correction function 122 is a function which associates the projection data obtained from the actual measured data (actual measured projection data) with the projection data being an ideal value after the BH correction (ideal projection data).

It is possible to configure such that the plotted result is displayed, for instance, on a display screen or the like for allowing a user to generate the approximate expression (the function A and the BH correction function 122), or the information processor generates the approximate expressions by using a program held in advance. Furthermore, as described above, the influence of the beam hardening is represented as μt, using the absorption coefficient μ and the transmission distance (thickness of the subject) t. Therefore, it is possible to configure such that instead of approximating the actual measurement projection data to calculate the function A, it is further possible to use, as the gradient of the function A, a theoretical value of the absorption coefficient μ or the absorption coefficient μ that is obtained in advance by a second device. As the second device, a general medical-use CT apparatus may be considered, which uses a line detector being known as having a small scattered X-ray amount, or a Ge detector may be also considered, for example. Use of the theoretical value or the absorption coefficient μ obtained by the second device in advance may eliminate the need for the processes in the steps S503 and S504, achieving speed-up of the processing.

In FIG. 8, it is further possible that an approximate curve, determined by fitting the plotted result of the projection data P ($c_0$, $x_j$) itself, is assumed as the function C ($c_0$, $x_j$). For this case, in FIG. 9, the horizontal axis shows C and the vertical axis shows A, and the approximate function is determined from the result of plotting, and the approximate function is assumed as the BH correction function 122.

Next, a procedure for generating the SX correction function will be explained. In here, the measurement system as shown in FIG. 7 uses m water cylinders having different diameters $x_j$ ($1 \le j \le m$) as the simulated subject, the collimator width c is changed for each of the water cylinders, and conducts the SX correction function generation measurement using n different collimator widths $c_i$ ("i" is a natural number between or equal to 1 and n, n is a natural number). It is desirable that the collimator width c being set includes the collimator width $c_0$ which realizes the specific scattered X-ray amount and/or the collimator width $c_a$ used in the actual measurement. Hereinafter, the collimator width $c_a$ used in the actual measurement is referred to as an actual collimator width $c_a$.

Figure 10:
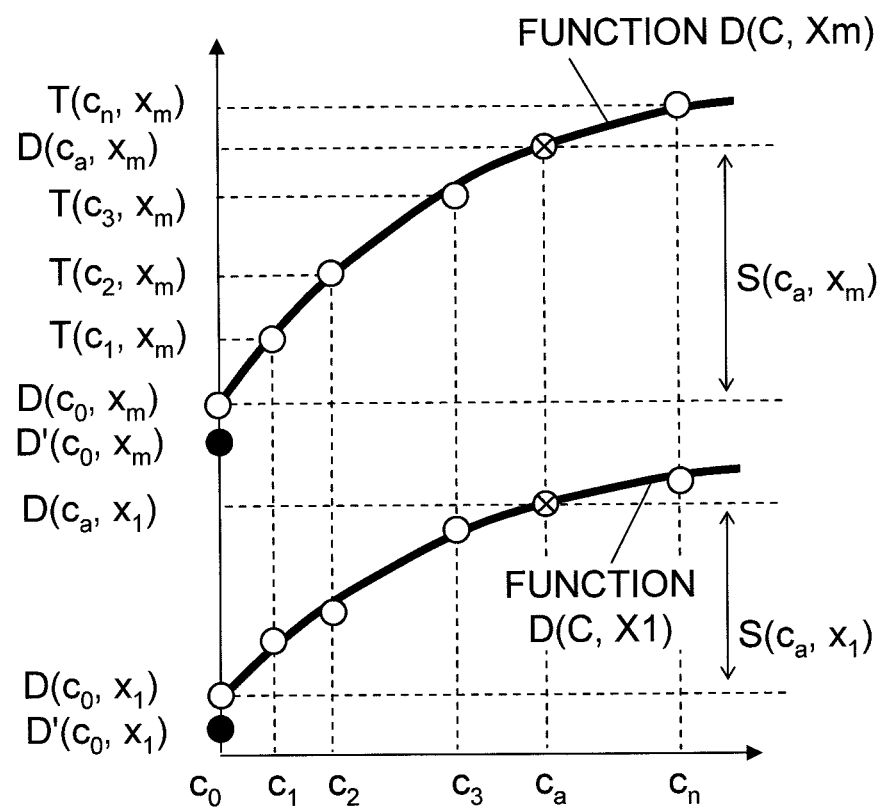
FIG. 10 is an illustration for explaining a method for deciding the scattered X-ray amount according to the first embodiment.

Each of the transmittance data items calculated from the measured data obtained by the SX correction function generating measurement are plotted as a measurement result on the graph showing the collimator width $c_i$ on the horizontal axis and showing the transmittance data T ($c_i$, $x_j$) on the vertical axis. FIG. 10 is a graph showing the plotted result.

Then, an approximate curve fitting each plotted result for each transmission distance $x_j$ is determined as a function D(c, $x_j$) ($1 \le j \le m$) for the collimator width c. On this occasion, a linear equation, a quadratic equation, a polynominal equation, a logarithm function, or the like, may be used as the approximate expression. It is possible to configure such that, for instance, the plotted result is displayed on a display screen or the like for allowing a user to generate the approximate expression, or the information processor generates the approximate expression by using a program held in advance.

The function D(c, $x_j$) ($1 \le j \le m$) is used to calculate, as to each measured position $x_j$, transmittance data D($c_a$, $x_j$) in the real collimator width $c_a$ and transmittance D($c_0$, $x_j$) in the specific collimator width $c_0$. It is to be noted that, for example, a value of the specific collimator width $c_0$ may be considered as 0 and a value of the intercept of the function D(c, $x_j$) ($1 \le j \le m$) on the vertical axis may be used.

Next, as to each transmission distance $x_j$, a difference value S($c_a$, $x_j$) is obtained by subtracting the transmittance data D($c_0$, $x_j$) (or the value of intercept) in the collimator width $c_0$ from the transmittance data D($c_a$, $x_j$) in the real collimator width $c_a$. Here, since the transmittance data D($c_0$, $x_j$) corresponds to nearly direct X-ray intensity, the aforementioned difference value S($c_a$, $x_j$) may indicate scattered X-ray intensity at the transmission distance $x_j$, for the collimator width $c_a$ (in the scattered X-ray amount) used in the real measurement.

Figure 11:
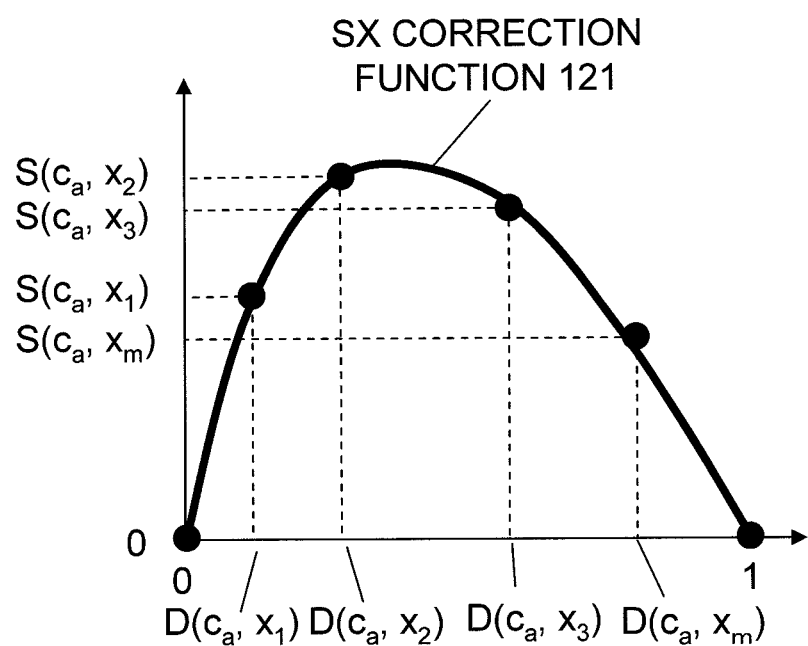
FIG. 11 is an illustration for explaining a method for deciding the scattered X-ray correction function according to the first embodiment.

As to each transmission distance $x_j$, the scattered X-ray intensity S($c_a$, $x_j$) is calculated, and it is plotted on the graph showing the transmittance data D($c_a$, $x_j$) in the real collimator width $c_a$ on the horizontal axis and showing the scattered X-ray intensity S($c_a$, $x_j$) on the vertical axis. FIG. 11 is a graph showing the plotted result. Here, since the scattered X-ray intensity becomes zero when there is no subject, it is possible to add data indicating D=1.0 and S=0.0. Furthermore, since the transmittance data becomes zero when the subject is extremely thick, it is possible to add data indicating D=0.0 and S=0.0. An approximate curve fitting the plotted result is determined, and it is assumed as the SX correction function 121. It is to be noted that a linear equation, a quadratic equation, a polynominal equation, a logarithm function, or the like, may be used as the approximate expression. By way of example, approximation can be performed according to the following formula (1):

$$S = D - D^{\frac{1}{1-k}} \quad (1)$$

In the formula (1), S represents the scattered X-ray intensity S($c_a$, $x_j$) in the collimator width $c_a$, D represents the transmittance data D($c_a$, $x_j$) in the collimator width $c_a$, and k represents a coefficient in the collimator width $c_a$ actually used at the time of real measurement. By fitting the plotted result with the formula (1), k is determined, and an approximate expression, i.e., the SX correction function 121 is completed.

As thus described, the scattered SX correction function 121 of the present embodiment associates the transmittance data obtained from the actual measured data, with the scattered X-ray intensity under the scattered X-ray amount condition at the time of actual measurement. The influence of the scattered X-rays is corrected by subtracting the scattered X-ray amount associated with the transmittance data, from the transmittance data being obtained.

The BH correction function 122 and the SX correction function 121 generated according to the procedure described above are held in the storage device of the X-ray imaging apparatus 200 of the present embodiment.

As discussed above, according to the present embodiment, the function for correcting the influence of the scattered X-rays and the function for correcting the influence of the beam hardening are prepared independently, thereby correcting the measured data being obtained. The SX correction function for correcting the scattered X-rays is used to obtain the scattered X-ray intensity associated with the transmittance data that is calculated from the obtained measured data. The BH correction function for correcting the influence of the beam hardening replaces the projection data calculated from the measured data being obtained, with an ideal value as to which the influence from the beam hardening is eliminated. Each of the functions can be realized according to a simple operation process. In particular, the BH correction function is configured in such a manner that the transmittance data is converted to projection data, and influence of the beam hardening according to the transmission distance is approximated by a straight line. Therefore, compared to the case where the processing is performed using the transmittance data without any conversion, it is possible to obtain a correction result with much higher precision.

According to the present embodiment, it is possible to realize each of the corrections with high precision, easily and at high speed. Consequently, it is possible to recover image contrast, and obtain a two-dimensional image or a three-dimensional reconstructed image with a high image quality having improved quantitativity of values.

In the present embodiment, both correction functions are used to correct the measured data, firstly by the scattered X-ray correction, and subsequently by the beam hardening correction. Adequate corrections can be performed respectively, and therefore it is possible to prevent over-corrections.

Furthermore, the BH correction function 122 and the SX correction function 121 can be calculated by the X-ray imaging apparatus 200 used for actual measurement. Therefore, it is possible to acquire optimum correction values suitable for a characteristic of the apparatus. Furthermore, these correction functions can be obtained, as described above, according to a simple operation process based on the measured data that is obtained by a simple measurement.

It is further possible to configure such that a process of judgment using a threshold is added to a result of the operation process, when the scattered X-ray intensity calculated by the SX correction function 121 is subtracted from the transmittance data, or when the BH correction function 122 corrects the projection data value, so as to avoid the case where a value after the correction becomes equal to or less than a predetermined value. In other words, the result of the operation is compared with the threshold, and when the operation result becomes smaller than the threshold, it is replaced by the threshold. It is alternatively possible to configure such that the result of the operation is compared with the threshold, and when the operation result becomes smaller than the threshold, a value, which is an average value obtained by using a result of neighborhood operation and also larger than the threshold, is assumed as the correction value. With the configuration as described above, the correction value may not become too small, thereby suppressing noises and reducing occurrence of artifact.

In the BH correction function generation measurement and/or the SX correction function generation measurement, the number of changes as to the collimator width c and the number of measured position x, which are considered to be sufficient, are two or more for each, because it is only required to obtain an approximate expression. There has been explained an example that the collimator width $c_0$ to realize the specific scattered X-ray amount condition is assumed as minimum collimator width ($\approx 0$). However, the specific collimator width $c_0$ is not limited to this value. It is possible to use any collimator width as far as the contained amount of scattered X-rays is small. By way of example, a collimator width for fan-beam CT measurement may be employed.

<<Second Embodiment>>

A second embodiment to which the present invention is applied will be explained. The X-ray imaging apparatus according to the present embodiment has basically the same configuration as the first embodiment. The BH correction function is also the same as that of the first embodiment. However, the SX correction function is different from that of the first embodiment. In the first embodiment, transmittance data is made to associate with scattered X-ray intensity to obtain the SX correction function. However, in the present embodiment, the transmittance data is made to associate with direct X-ray intensity to obtain the SX correction function.

A procedure for generating the SX correction function 121' according to the present embodiment will be explained. The procedure for generating the SX correction function 121' according to the present embodiment is basically the same as the procedure of the first embodiment as shown in FIG. 6. It is to be noted that since the transmittance data is associated with the direct X-ray intensity, in the step S604, the transmittance data under the condition of the specific scattered X-ray amount is used as it is, to be used as a correction value. Then, the processing proceeds in the same manner as described, and a function that associates multiple correction values being obtained, with the transmittance data items at the time of real measurement, is assumed as the SX correction function 121' according to the present embodiment.

A specific procedure for generating the correction function 121' of the present embodiment is as the following. The SX correction function generation measurement is performed in the same manner as the first embodiment, and based on a resulting graph (FIG. 10), an approximate curve fitting the plotted result for each transmission distance $x_j$, is determined as the function $D(c, x_j)$ using the collimator width c as a variable. Then, by using the function $D(c, x_j)$, the transmittance data $D(c_a, x_j)$ in the real collimator width $c_a$ and the transmittance data $D(c_0, x_j)$ in a specific collimator width $c_0$ are calculated as to each measured position $x_j$. Also in the present embodiment, for instance, a value of the specific collimator width $c_0$ may be considered as 0, and a value of intercept on the vertical axis of the function $D(c, x)$ may be used. Here, the transmittance data $D(c_0, x_j)$ in the specific collimator width $c_0$ may be treated as nearly direct X-ray intensity.

Figure 12:
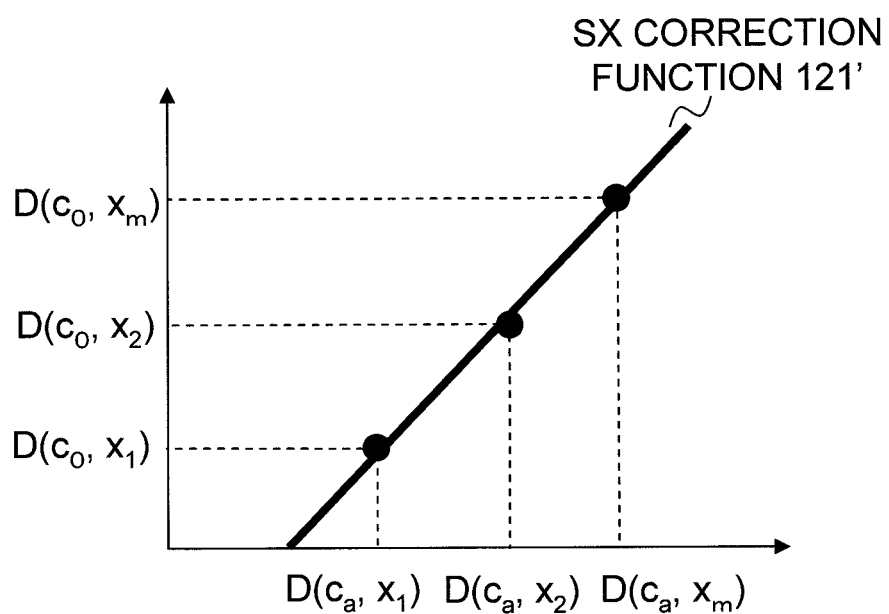
FIG. 12 is an illustration for explaining a method for deciding the scattered X-ray correction function according to the second embodiment.

As to each transmission distance $x_j$, plotting is performed on a graph showing the transmittance data $D(c_a, x_j)$ in the real collimator width $c_a$ on the horizontal axis, and showing the direct X-ray intensity $D(c_0, x_j)$ on the vertical axis. FIG. 12 is a graph showing the plotted result. An approximate curve fitting this plotted result is determined, and it is assumed as the SX correction function 121'. It is to be noted that a linear equation, a quadratic equation, a polynominal equation, a logarithm function, or the like, may be used as the approximate expression.

As thus described, the SX correction function 121' of the present embodiment associates the transmittance data obtained from actual measured data, with the direct X-ray intensity under the scattered X-ray amount condition at the time of actual measurement. Also in the present embodiment, the SX correction function 121' is held by the storage device of the X-ray imaging apparatus 200.

Figure 13:
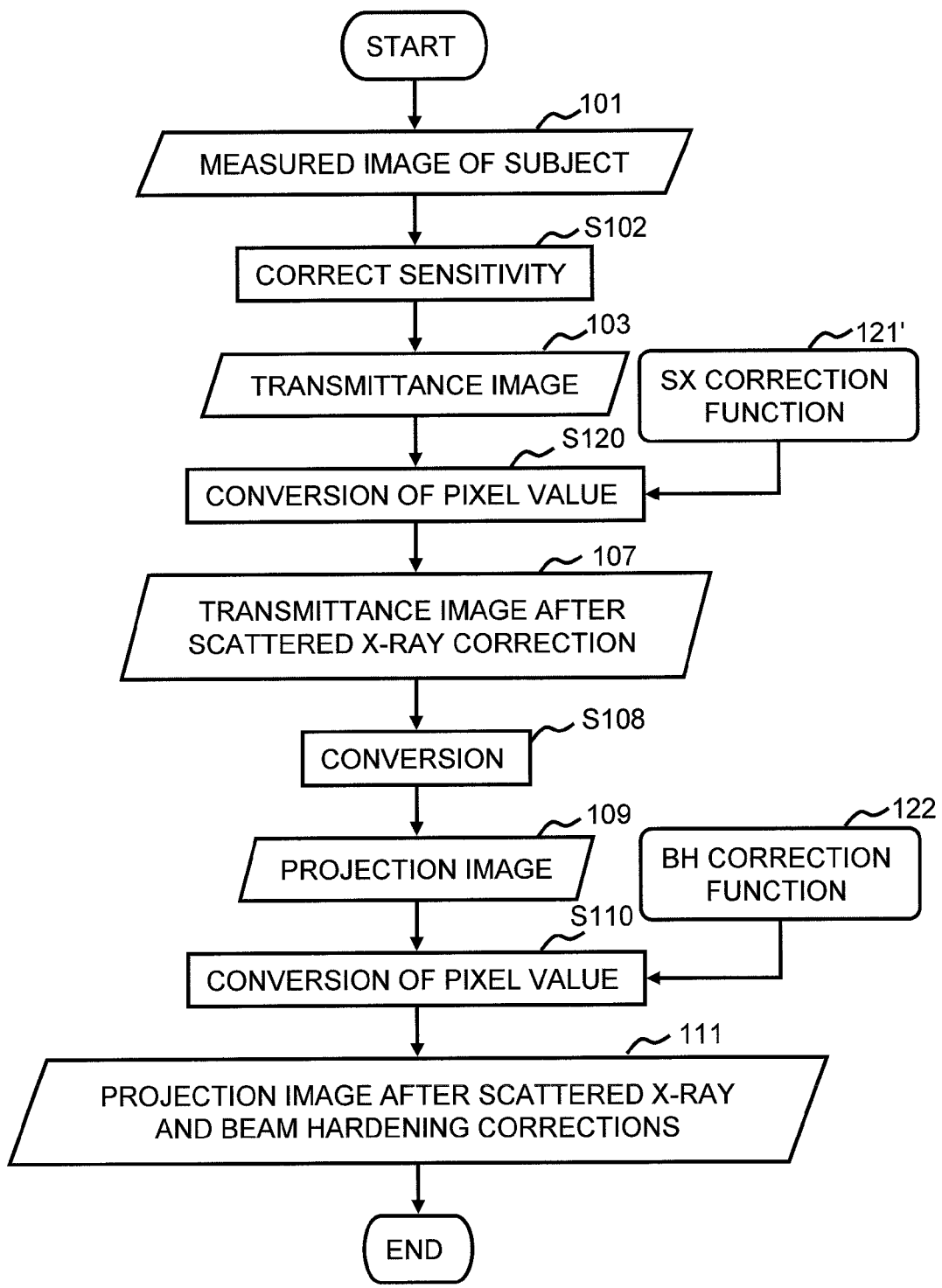
FIG. 13 is a flow of the correction process according to the second embodiment.

Hereinafter, a flow of the correction process will be explained, when the SX correction function 121' the present embodiment is used. FIG. 13 is a flow of the correction process according to the correction processing section of the present embodiment. This process is basically the same as the flow of the correction process according to the first embodiment as shown in FIG. 4. However, the procedure for correcting the scattered X-rays is different. In other words, instead of the processing of the steps S104 and 5106, the SX correction function 121' is used to obtain the data after the scattered X-ray correction (scattered X-ray correction image) 107, directly from the transmittance data (transmittance image) 103 (step S120). Subsequent processing is the same as the processing of the first embodiment as shown in FIG. 4.

Also in the present embodiment, the SX correction function 121' and the BH correction function 122 used for the correction process described above are obtained from the data that is measured in advance by using a simulated subject. The processes for generating these correction functions are performed at the timing designated as the implementation mode in the aforementioned correction function generation process. By way of example, the processes may be performed as a pre-measurement immediately before the real measurement, or they may be performed independently of the real measurement, such as performing at the time when the X-ray imaging apparatus 200 is installed. The correction function generation process is realized when the CPU executes an operation process according to a program in the information processor. It is possible to configure such that the controller 206 also serves as the information processor, or the information processor may be provided independently of the X-ray imaging apparatus 200.

Also in the present embodiment, similar to the first embodiment, it is possible to add a judgment using a threshold when the transmittance data is converted by using the SX correction function 121'. The number of changes as to the collimator width c, the number of transmission distances x, and the specific collimator width $c_0$ are the same as the first embodiment.

As discussed above, according to the present embodiment, a relational expression between the transmittance data and the direct X-ray intensity is used as a correction function, in correcting the influence of the scattered X-rays. Therefore, it is possible to reduce the processing steps compared to the first embodiment. Accordingly, in addition to the effect obtained by the first embodiment, a higher speed processing can be realized.

In calculating the SX correction functions 121 and 121' according to the first and second embodiments, the transmittance data $D(c_a, x_j)$, the correction value $D(c_0, x_j)$, and the correction value $S(c_a, x_j)$ may be replaced by an average value of each, $D_{AVR}(c_a, x_j)$, $D_{AVR}(c_0, x_j)$, or $S_{AVR}(c_a, x_j)$. The average value is obtained from multiple data items of each data above, acquired by measuring the same simulated subject more than once. Alternatively, it is obtained from each of the above data of all pixels on one transmittance image, or from multiple data items of each data above within arbitrary region being set on one transmittance image. By using the average value, it is possible to improve the precision of approximate expression, and accordingly the precision of correction is also enhanced.

Hereinafter, there will be explained a procedure to obtain the SX correction functions 121 and 121' by using the average value of data such as transmittance data. Here, an explanation will be made taking an example that the average value is obtained from multiple data items of each data above within the arbitrary region being set on one transmittance image. Collimator width c is changed from $c_1, c_2, c_i$, to $c_n$, and as to each case, a water cylinder with a diameter of $x_j$ is subjected to measurement to obtain m×n transmittance images. It is to be noted here that the transmittance data as to all the transmission distances may be obtained every time when the collimator width c is changed, or every time when the transmission distance x is changed, the transmittance data as to all the collimator widths c may be obtained.

A region of arbitrary size is defined on each of the transmittance images, and an average value $T_{AVR}(c_i, x_j)$ of the transmittance data $T(c_i, x_j)$ within the region is obtained for each image. By way of example, the size of the region may be set to a specific collimator width $c_0$. The result is plotted on a graph showing the collimator width c on the horizontal axis and showing the average transmittance data $T_{AVR}(c_i, x_j)$ on the vertical axis so as to obtain an approximate expression D, and the average transmittance data $D_{AVR}(c_a, x_j)$ in the collimator width $c_a$ at the time of measurement and the average transmittance data $D_{AVR}(c_0, x_j)$ in the specific collimator width $c_0$ are calculated. Also in here, an intercept may be used as the average transmittance data $D_{AVR}(c_0, x_j)$. Hereinafter, in the same procedure as the embodiment described above, a combination of the average transmittance data and the correction value for each diameter $x_j$, $(D_{AVR}(c_a, x_j) D_{AVR}(c_0, x_j))$ or $(D_{AVR}(c_a, x_j), S_{AVR}(c_a, x_j))$ is obtained.

By way of example, according to the same procedure as that of the first embodiment described above, approximation is performed by the following formula (2), based on the combination of the average transmittance data and the correction value $(D_{AVR}(c_a, x_j) S_{AVR}(c_a, x_j))$ and this is assumed as the SX correction function 121".

$$S_{AVR} = D_{AVR} - (D^{\frac{1}{1-k}})_{AVR} \quad (2)$$

In the formula (2) above, $S_{AVR}$ represents $S_{AVR}(c_a, x_j)$, $D_{AVR}$ represents $D_{AVR}(c_a, x_j)$, and k represents a coefficient in the collimator width $c_a$.

In the procedure above, if an average value obtained from all the pixels on one transmittance image is employed, identical values can be used as the scattered X-ray intensity $S(x)_{AVR}$ and the direct X-ray intensity $D(x)_{AVR}$ for all the pixels on the transmittance image. Therefore, it is possible to achieve further speed-up of the processing.

It is further possible that the transmittance image is divided into multiple regions, and each of the correction values $S_{AVR}$, $D_{AVR}$ is calculated as an average value of pixels within each of the regions. For this case, the correction values $S_{AVR}$, $D_{AVR}$ are values different for each of the regions, and thus, corrections can be performed with an optimum correction value for each region, thereby enhancing precision of correction. In this case above, if the correction value is smoothed in proximity to a boundary of the regions, it is possible to avoid occurrence of gap in the correction image on the boundary of regions. The smaller is the divided region, the higher the precision of correction is enhanced. In addition, this enables handling of local fluctuations, thereby achieving high precision in correcting the subject having a complicated structure. It is further possible to configure such that the region is divided in units of one pixel.

It is further possible to obtain the correction value by using an average value acquired from all the pixels of the transmittance image, and the correction values $S_{AVR}$, $D_{AVR}$ are calculated, being weighted according to a position on the transmittance image. Then, the correction values which vary depending on the position on the transmittance image are used to enhance the precision. In the case above, for example, the weight is obtained as a ratio of the scattered X-ray intensity or the direct X-ray intensity calculated by dividing the transmittance image into multiple regions, to the correction value calculated from all the pixels of the transmittance image on an arbitrary subject.

It is further possible to configure such that the obtained transmittance data is subjected to weighting addition average by surrounding data, thereby generating blurring transmittance data, and the correction value may be calculated by using a value of the blurring transmittance data. It is alternatively possible to configure such that the correction value is subjected to the weighting addition averaging by the surrounding data, thereby calculating the blurring correction value. By using the blurring transmittance data or the blurring correction value, it is possible to prevent the correction value from becoming an exceptional value, in the case where a noise or the like causes a peculiar value of transmittance data. In addition, since the correction value does not become too small or too large, it is possible to prevent increase of noise or occurrence of artifact in the correction image. It is further possible to configure such as adding a condition that when a value of the transmittance data is smaller than a threshold, the blurring transmittance data is used. With the configuration above, it is possible to perform the correction with high precision, while preventing increase of noise and occurrence of artifact. In the first embodiment, a condition is added where the blurring transmittance data is used when the correction value is larger than the threshold, thereby enabling the highly precise correction, while preventing increase of noise and occurrence of artifact. In the second embodiment, a condition is added where the blurring transmittance data is used when the correction value is smaller than the threshold, thereby enabling the highly precise correction, while preventing increase of noise and occurrence of artifact.

<<Third Embodiment>>

Next, a third embodiment to which the present invention is applied will be explained. The X-ray imaging apparatus of the present embodiment has basically the same configuration as each of the aforementioned embodiments. In each of the embodiments, the correction of scattered X-ray and the correction of influence caused by beam hardening are independently performed by using the SX correction function and the BH correction function, respectively. However, in the present embodiment, the correction for beam hardening is incorporated in the SX correction function. Accordingly, the correction of the measured data by using only the SX correction function achieves both the scattered X-ray correction and the beam hardening correction on the measured data after the scattered X-ray correction is performed. Hereinafter, with regard to the present embodiment, the SX correction function 123 that has a configuration different from each of the aforementioned embodiments and a correction process that uses the SX correction function 123 will be explained.

A procedure for generating the SX correction function 123 of the present embodiment is basically the same as the procedure for generating the SX correction function 121 of the first embodiment shown in FIG. 6. However, a value employed as the correction value in the step S604 is different. In the first embodiment, the scattered X-ray amount $S(c_a, x_j)$ obtained by subtracting the transmittance data $D(c_0, x_j)$ as shown in FIG. 10 from the transmittance data $D(c_a, x_j)$ is associated with the correction value of the transmittance data $D(c_a, x_j)$. In the present embodiment, a scattered X-ray amount calculated by using data $D'(c_0, x_j)$, which is obtained by additionally performing the beam hardening correction on the transmittance data $D(c_0, x_j)$, is assumed as the correction value.

Specifically, in FIG. 10, the transmittance data $D(c_0, x_j)$ corresponding to the specific scattered X-ray amount, having the same transmission distance as the transmittance data $D(c_a, x_j)$ is converted into projection data $P(c_0, x_j)$. Then, this projection data $P(c_0, x_j)$ is corrected by using the BH correction function 122, thereby obtaining a value $A(c_0, x_j)$ after the correction. $A(c_0, x_j)$ is converted into the transmittance data $D'(c_0, x_j)$, and this transmittance data $D'(c_0, x_j)$ is assumed as the transmittance data corresponding to the specific scattered X-ray amount according to the present embodiment. It is to be noted that when the projection data P is converted into the transmittance data T, the projection data P is multiplied by (−1), and then it is subjected to the Exp conversion.

The scattered X-ray amount $S'(c_a, x_j)$ after the beam hardening correction is calculated, by subtracting the transmittance data $D'(c_0, x_j)$ from the transmittance data $D(c_a, x_j)$. Then, the calculation result is plotted on a graph showing the transmittance data $D(c_a, x_j)$ in the real collimator width $c_a$ on the horizontal axis, and showing the scattered X-ray intensity $S'(c_a, x_j)$ after the beam hardening correction on the vertical axis, and then an approximate curve fitting the plotted result is assumed as the SX correction function. It is to be noted that a linear equation, a quadratic equation, a polynominal equation, a logarithm function, or the like, may be used as the approximate expression. In addition, the formula (1) as describe above may be used, for instance.

Figure 14:
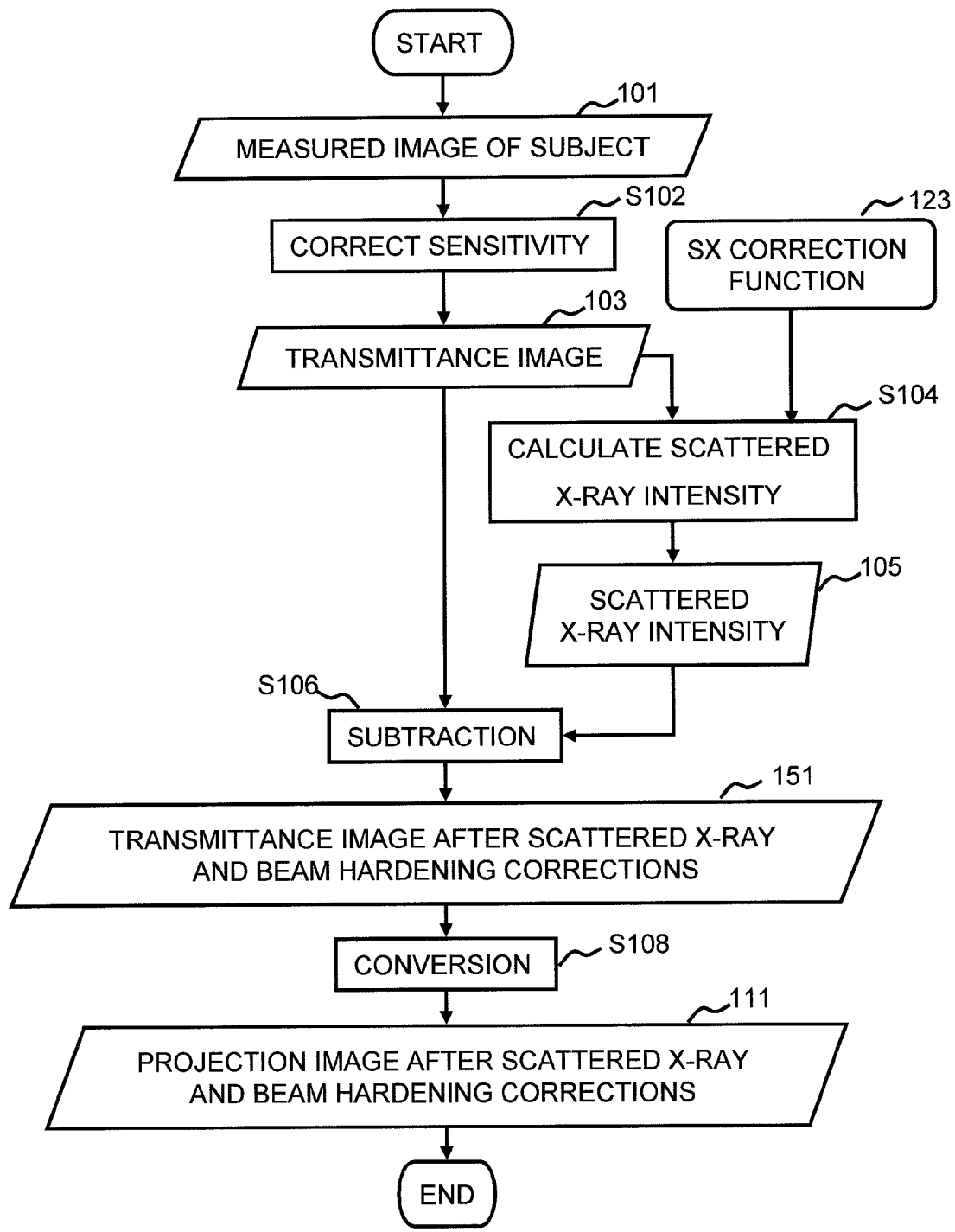
FIG. 14 is a flow of the correction process according to the third embodiment.

Hereinafter, an explanation will be made as to a flow of the correction process in the case where the correction function 123 according to the present embodiment is used. FIG. 14 is a flow of the correction process according to the correction processing section of the present embodiment. The correction process of the present embodiment is basically the same as the correction process of the first embodiment as shown in FIG. 4. However, in the scattered X-ray intensity 105 calculated by using the SX correction function 123 in the step S104, the influence of the beam hardening has already been corrected. Therefore, by the subtraction (step S106), it is possible to obtain a transmittance image 151 which has already been subjected to the scattered X-ray correction and the beam hardening correction. The transmittance image 151 being obtained is converted (step S108) to obtain a projection image 111 on which the scattered X-ray correction and the beam hardening correction are performed.

As discussed above, according to the present embodiment, one SX correction function 123 enables the beam hardening correction and the scattered X-ray correction with high precision similar to the first embodiment. Therefore, in addition to the effect obtained by the first embodiment, it is possible to further speed up the processing. The SX correction function 123 can be easily generated from the measured data that is acquired in a simple manner as described above. Therefore, it is possible to achieve the effect as described above, without adding a complicated configuration.

It is to be noted that the correction process according to the present embodiment can be applied to the correction using the direct X-rays, in the same manner as the second embodiment. In other words, the correction value of the transmittance data $D(c_a, x_j)$ calculated from the function D above is assumed as a value $D'(c_0, x_j)$, which is obtained according to the above procedure, by subjecting the transmittance data $D(c_0, x_j)$ corresponding to the specific scattered X-ray amount calculated from the function D to the beam hardening correction. Then, the result is plotted on a graph showing the transmittance data $D(c_a, x_j)$ in the real collimator width $c_a$ on the horizontal axis, and showing the transmittance data $D'(c_0, x_j)$ after the beam hardening correction is performed on the vertical axis, and then an approximate curve fitting the plotted result is assumed as the SX correction function 123'. It is to be noted that a linear equation, a quadratic equation, a polynominal equation, a logarithm function, or the like, may be used as the approximate expression.

Figure 15:
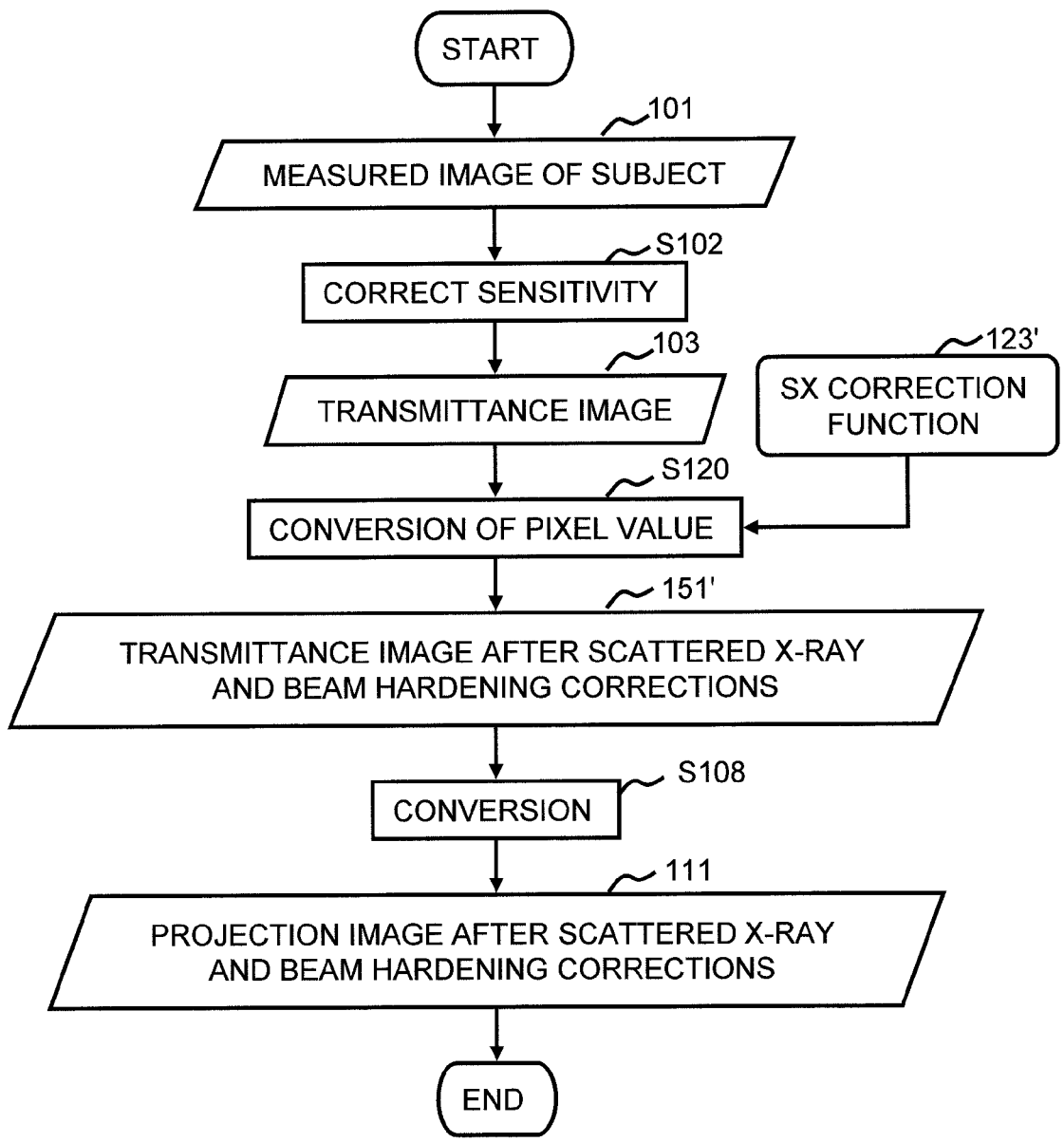
FIG. 15 is another example of the flow of the correction process according to the third embodiment.

An explanation will be made as to a flow of the correction process in the case where the SX correction function 123' according to the present embodiment is used. FIG. 15 is a flow of the correction process according to the correction processing section in this example. The correction process in the example here is basically the same as the correction process according to the second embodiment shown in FIG. 13. However, similar to the case above, the transmittance data calculated by using the SX correction function 123' in the step S120 has already been subjected to the beam hardening correction. Therefore, as a result of the conversion in the step S120, it is possible to obtain a transmittance image 151' already subjected to the scattered X-ray correction and the beam hardening correction. The transmittance image 151' being obtained is converted (step S108), and the projection image 111 is obtained on which the scattered X-ray correction and the beam hardening correction are performed.

According to the present embodiment, one SX correction function 123' enables the beam hardening correction and the scattered X-ray correction with high precision similar to the second embodiment. Therefore, in addition to the effect obtained by the second embodiment, it is possible to further speed up the processing. The SX correction function 123' can be easily generated from the measured data that is acquired in a simple manner as described above. Therefore, it is possible to achieve the effect as described above, without adding a complicated configuration.

It is to be noted that in the present embodiment, a method for realizing the specific collimator width $c_0$, the number of changes as to the collimator width c in the measurement, and the number of the transmission distance x, are same as each of the above embodiments. Similar to each of the above embodiments, various modifications are possible, such as adding the judgment by a threshold, using an average value, and performing the weighting addition averaging process.

<<Fourth Embodiment>>

Next, there will be explained a fourth embodiment to which the present invention is applied. The X-ray imaging apparatus of the present embodiment has basically the same configuration as each of the embodiments above. Also in the present embodiment, similar to the third embodiment, the beam hardening correction is incorporated in the SX correction function, and one-time conversion process achieves both the scattered X-ray correction and the beam hardening correction. In the third embodiment, correction is performed on the transmittance data, but in the present embodiment, the correction is performed after converted into the projection data. Hereinafter, as to the present embodiment, the SX correction function 124 and the correction process using the SX correction function 124, having a configuration different from each of the embodiments above, will be explained.

A procedure for generating the SX correction function 124 of the present embodiment is basically the same as the procedure for generating the SX correction function 121' of the second embodiment. It is to be noted here that before plotting on the graph as shown in FIG. 10, the transmittance data is converted into the projection data. After the conversion into the projection data, plotting on the graph is performed, and an approximate curve fitting each plotted result is determined as the function $E(c, x_j)$ using the collimator c as a variable, with respect to each transmission distance $x_j$.

In addition, the projection data $P(c_0, x_j)$ obtained from the transmittance data in the specific collimator width $c_0$ is corrected by the BH correction function, thereby obtaining projection data $P'(c_0, x_j)$ in the specific collimator width $c_0$ after the beam hardening correction is performed. On the other hand, the projection data $P(c_a, x_j)$ in the real collimator width $c_a$ is obtained from the approximate curve E. A curve obtained by approximating the plotted result of a combination of $P'(c_0, x_j)$ and $P(c_a, x_j)$ with respect to each transmission distance $x_j$ is assumed as the SX correction function 124 of the present embodiment. It is to be noted that a linear equation, a quadratic equation, a polynominal equation, a logarithm function, or the like, may be used as the approximate expression.

As thus described, the SX correction function 124 of the present embodiment associates the projection data obtained from real measured data, with the projection data from which the scattered X-rays are eliminated under the scattered X-ray amount condition at the time of actual measurement and on which the beam hardening correction is performed. Therefore, only the SX correction function 124 enables both the scattered X-ray correction and the beam hardening correction to be performed.

Figure 16:
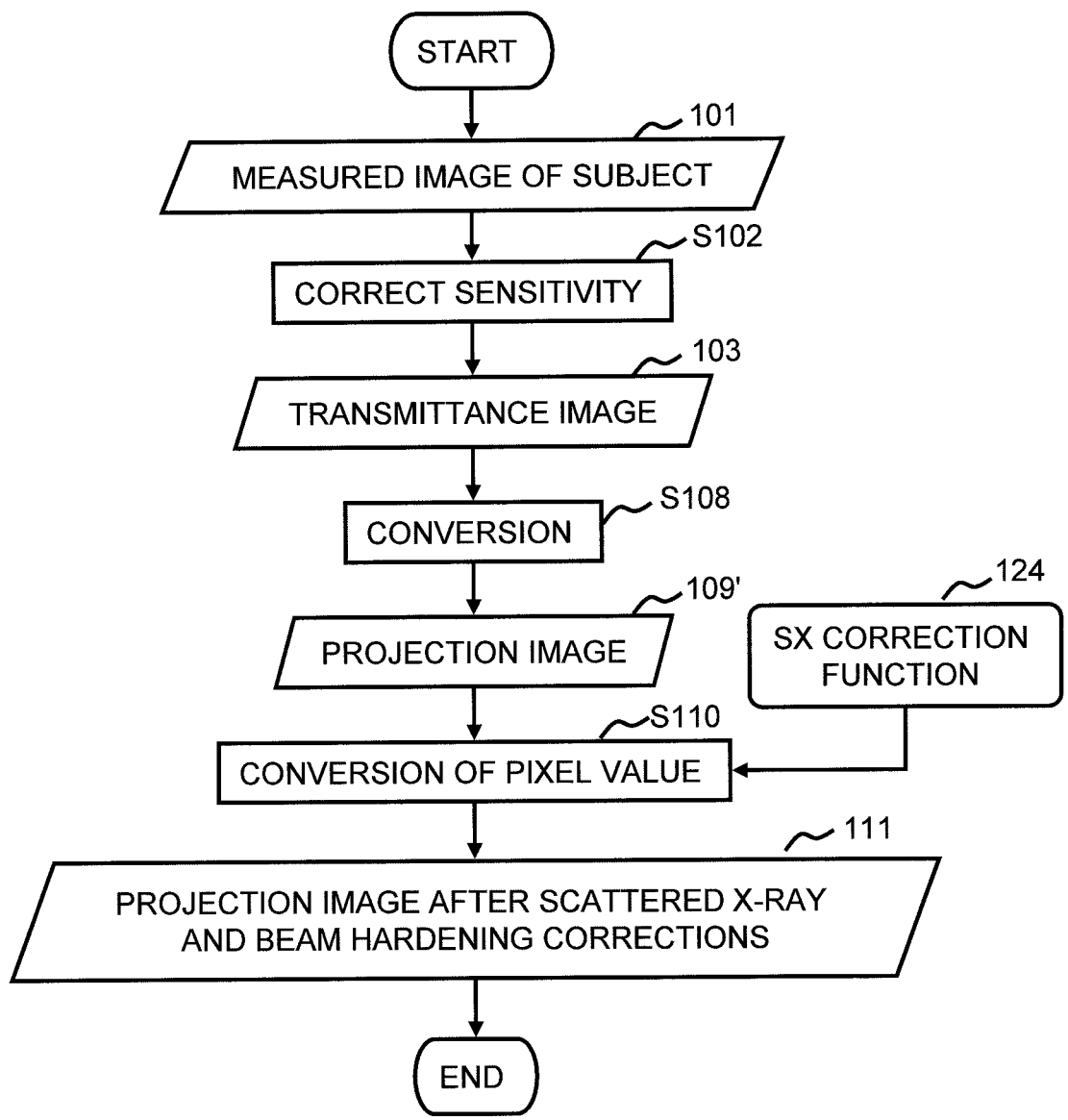
FIG. 16 is a flow of the correction process according to the fourth embodiment.

It is to be noted here that as described above, since the correction function is for the projection data, the flow of the correction process by the correction processing section in the case where the SX correction function 124 is used according to the present embodiment becomes the flow as shown in FIG. 16. The correction process here is basically the same as the correction process of the second embodiment as shown in FIG. 13. However, after the transmittance data (transmittance image) 130 is converted into the projection data (projection image) 109' (step S108), influences of the scattered X-ray and the beam hardening are corrected by using the SX correction function 124 of the present embodiment. Then, the projection image 111, which has been subjected to the scattered X-ray correction and the beam hardening correction, is obtained.

According to the present embodiment, one SX correction function 124 enables the beam hardening correction and the scattered X-ray correction with high precision similar to the second embodiment. Therefore, in addition to the effect obtained by the second embodiment, it is possible to further speedup the processing. In addition, it is possible to easily generate the SX correction function 124 from the measured data which can be acquired simply as described above. Therefore, it is possible to achieve the effect as described above, without adding a complicated configuration.

It is to be noted that in the present embodiment, a method for realizing the specific collimator width $c_0$, the number of changes as to the collimator width c in the measurement, and the number of the transmission distance x, are the same as each of the above embodiments. Similar to each of the above embodiments, various modifications are possible, such as adding the judgment by a threshold, using an average value, and performing the weighting addition averaging process.

<<Fifth Embodiment>>

Next, the fifth embodiment to which the present invention is applied will be explained. The X-ray imaging apparatus of the present embodiment has basically the same configuration as each of the above embodiments. Similar to the third and the fourth embodiments, in the present embodiment, the beam hardening correction is incorporated in the SX correction function, and one-time conversion process achieves the scattered X-ray correction and the beam hardening correction. However, in the present embodiment, the SX correction function indicates a function where the transmittance data is associated with the projection data after the scattered X-ray correction and the beam hardening correction are performed. Hereinafter, an explanation will be made as to the SX correction function 125 and the correction process using the SX correction function 125, having a configuration different from each of the embodiments.

In the present embodiment, the measured data acquired by changing the collimator width c and the transmission distance $x_j$ is plotted as shown in FIG. 10, in the same manner as each of the first and the second embodiments, and the function $D(c, x_j)$ is obtained which uses the collimator width c as a variable, with respect to each transmission distance $x_j$. By using the function D, the transmittance data $D(c_a, x_j)$ in the real collimator width $c_a$ and the transmittance data $D(c_0, x_j)$ in the specific collimator width $c_0$ are obtained, with respect to each transmission distance $x_j$. In here, a value of intercept of the function D may be used as the $D(c_0, x_j)$.

$D(c_0, x_j)$ is converted into the projection data $F(c_0, x_j)$, and it is corrected by the BH correction function 122, thereby acquiring the projection data $F'(c_0, x_j)$ after the beam hardening correction is performed. A combination of $F'(c_0, x_j)$ and $D(c_a, x_j)$ is plotted, which are acquired for each transmission distance, and the plotted result is approximated to obtain a curve that is assumed as the SX correction function 125 of the present embodiment. It is to be noted that a linear equation, a quadratic equation, a polynominal equation, a logarithm function, or the like, may be used as the approximate expression.

As thus described, the SX correction function 125 of the present embodiment associates the transmittance data obtained from the actual measured data, with the projection data from which the scattered X-rays corresponding to the scattered X-ray amount at the time of actual measurement are eliminated, and on which the beam hardening correction is performed. Therefore, only the SX correction function 125 enables both the scattered X-ray correction and the beam hardening correction.

FIG. 17 shows a flow of the correction process in the case where the SX correction function 125 is used in the present embodiment. The correction process here is basically the same as the correction process of the second embodiment as shown in FIG. 13. However, conversion of pixel values (step S110) is performed as to the transmittance data (transmittance image) 103 according to the SX correction function 125 of the present embodiment, thereby obtaining a projection image 111 after the scattered X-ray correction and the beam hardening correction are performed.

According to the present embodiment, one SX correction function 125 performs the beam hardening correction and the scattered X-ray correction with high precision similar to the second embodiment, and in addition, the transmittance data is converted into the projection data within the SX correction function 125, thereby eliminating the logarithmic conversion in the correction process. Therefore, it is possible to speed up the processing, faster than the third embodiment and the forth embodiment.

It is to be noted that in the present embodiment, a method for realizing the specific collimator width $c_0$, the number of changes as to the collimator width c in the measurement, and the number of the transmission distance x, are same as each of the above embodiments. Similar to each of the above embodiments, various modifications are possible, such as adding the judgment by a threshold, using an average value, and performing the weighting addition averaging process.

It is to be noted that in each of the embodiments above, the scattered X-ray amount is made to vary by changing the collimator width c. However, a method for varying the scattered X-ray amount is not limited to this example. The scattered X-ray amount generated from the simulated subject varies according to the area of a region which is irradiated with X-rays. Therefore, it is only required to change the area of the region which is irradiated with X-rays. For example, it is possible to employ a method such as changing the area of the collimator. Instead of changing the area of the region irradiated with X-rays, it is further possible to change energy amount of X-rays to be irradiated by changing the scattered X-ray amount.

It is alternatively possible to configure such that only one of the corrections is performed; either the beam hardening correction according to the BH correction function or the scattered X-ray correction according to the SX correction function.

In addition, each of the above embodiments may not be limited to the measurement by X-rays, but it is applicable to all the measurements which generate scattered radiation components, such as light and radiation.

Denotation of Reference Numerals

121: SX CORRECTION FUNCTION, 121': SX CORRECTION FUNCTION, 122: BH CORRECTION FUNCTION, 123: SX CORRECTION FUNCTION, 123': SX CORRECTION FUNCTION, 124: SX CORRECTION FUNCTION, 125: SX CORRECTION FUNCTION, 200: X-RAY IMAGING APPARATUS, 201: X-RAY SOURCE, 202: DETECTOR, 203: SUPPORT, 204: ROTATION DEVICE, 205: SUBJECT HOLDER, 206: CONTROL PROCESSOR, 207: ROTATION AXIS, 208: SUBJECT, 210: GRID, 211: COLLIMATOR, 300: X-RAY IMAGING APPARATUS, 400: X-RAY IMAGING APPARATUS, 710: COLLIMATOR, 711: SHIELDING PLATE, 712: SHIELDING PLATE, 720: SIMULATED SUBJECT, 730: MEASURED IMAGE

What is claimed is:

1. A radiation imaging apparatus, comprising:
a radiation source for irradiating a subject with radiation;
a detector having multiple pixels for detecting the radiation;
a storage means for storing a scattered radiation correction function for correcting influence of scattered radiation on a detection result obtained from the detector, and a beam hardening correction function for correcting influence of beam hardening on the corrected detection result; and
a correction means for correcting the detection result by the scattered radiation correction function, and for correcting the corrected detection result by the beam hardening correction function,
wherein the scattered radiation correction function is calculated by using data measured with changes in a transmission distance and with changes in a scattered radiation amount, and returns a correction value of the scattered radiation amount in response to the detection result,
wherein the scattered radiation correction function is obtained by approximating a relation between a first transmittance data item corresponding to a first scattered radiation amount obtained from a first function that approximates a relation between the transmittance data and the scattered radiation amount with respect to each transmission distance, and a difference value obtained by subtracting the transmittance data when the scattered radiation amount obtained from the first function is nearly zero, from the first transmittance data item, and
wherein the correction means converts the detection result detected by the detector using the first scattered radiation amount, into the transmittance data, and corrects the influence of the scattered radiation by subtracting the correction value calculated from the transmittance data from the transmittance data.

2. The radiation imaging apparatus according to claim 1, wherein the beam hardening correction function is calculated by using data measured with changes in a transmission distance, and returns a beam hardening correction value in response to the corrected detection result after correcting the influence of the scattered radiation.

3. The radiation imaging apparatus according to claim 2, wherein the beam hardening correction function is a linear function passing through an original point, obtained by approximating a relation between a first projection data item obtained by converting the detection result measured with changes in the transmission distance when a scattered radiation amount is set to be nearly zero, and a second projection data item calculated from a function that returns a beam hardening amount in accordance with the transmission distance, and
wherein the correction means corrects transmittance data obtained from the detection result from the detector using the scattered radiation correction function, then converts the corrected transmittance data into a third projection data item, and replaces the third projection data item by the beam hardening correction value associated with the third projection data item, thereby correcting the influence of the beam hardening.

4. The radiation imaging apparatus according to claim 1, wherein the scattered radiation correction function is expressed by:

$$S_{AVR} = D_{AVR} - (D^{\frac{1}{1-k}})_{AVR}$$

where:
S represents the difference value,
D represents the first transmittance data,
k represents a coefficient, and
the suffix AVR represents an average value.

5. The radiation imaging apparatus according to claim 1, further comprising;
a collimator for adjusting an amount of radiation on the subject,
wherein the collimator is adjusted to have a collimator condition of a fan beam computed tomography (CT), so as to establish a state that the scattered radiation amount is nearly zero.

6. The radiation imaging apparatus according to claim 1, further comprising;
a correction function calculation means for calculating at least one of the scattered radiation correction function and the beam hardening correction function, respectively from the detection result.

7. The radiation imaging apparatus according to claim 1, further comprising
a controller for moving the radiation source and the detector relative to the subject; and
a reconstruction processor for reconstructing an image from the corrected detection result,
wherein the controller rotates the radiation source and the detector relative to the subject, and
wherein the reconstruction processor performs a reconstructing operation by using the corrected detection result to acquire a three-dimensional image.

8. The radiation imaging apparatus according to claim 1, further comprising;
a collimator for adjusting an amount of radiation on the subject,
wherein the scattered X-ray radiation amount is changed by changing a width between shielding plates forming the collimator.

9. A radiation imaging apparatus, comprising:
a radiation source for irradiating a subject with radiation;
a detector having multiple pixels for detecting the radiation;
a storage means for storing a scattered radiation correction function for correcting influence of scattered radiation on a detection result obtained from the detector, and a beam hardening correction function for correcting influence of beam hardening on the corrected detection result; and
a correction means for correcting the detection result by the scattered radiation correction function, and for correcting the corrected detection result by the beam hardening correction function,
wherein the scattered radiation correction function is calculated by using data measured with changes in a transmission distance and with changes in a scattered radiation amount, and returns a correction value of the scattered radiation amount in response to the detection result,
wherein the scattered radiation correction function is obtained by approximating a relation between a first transmittance data item corresponding to a first scattered radiation amount obtained from a first function that approximates a relation between the transmittance data and the scattered radiation amount with respect to each transmission distance, and a second transmittance data when the scattered radiation amount obtained from the first function is nearly zero, and
wherein the correction means converts the detection result detected by the detector using the first scattered radiation amount, into the transmittance data, and corrects the influence of the scattered radiation by replacing the transmittance data with the correction value calculated from the transmittance data.

10. The radiation imaging apparatus according to claim 9, wherein the beam hardening correction function is calculated by using data measured with changes in a transmission distance, and returns a beam hardening correction value in response to the corrected detection result after correcting the influence of the scattered radiation.

11. The radiation imaging apparatus according to claim 10,
wherein the beam hardening correction function is a linear function passing through an original point, obtained by approximating a relation between a first projection data item obtained by converting the detection result measured with changes in the transmission distance when a scattered radiation amount is set to be nearly zero, and a second projection data item calculated from a function that returns a beam hardening amount in accordance with the transmission distance, and
wherein the correction means corrects transmittance data obtained from the detection result from the detector using the scattered radiation correction function, then converts the corrected transmittance data into a third projection data item, and replaces the third projection data item by the beam hardening correction value associated with the third projection data item, thereby correcting the influence of the beam hardening.

12. The radiation imaging apparatus according to claim 9, further comprising:
a collimator for adjusting an amount of radiation on the subject,
wherein the collimator is adjusted to have a collimator condition of a fan beam computed tomography (CT), so as to establish a state that the scattered radiation amount is nearly zero.

13. The radiation imaging apparatus according to claim 9, further comprising:
a correction function calculation means for calculating at least one of the scattered radiation correction function and the beam hardening correction function respectively from the detection result.

14. The radiation imaging apparatus according to claim 9, further comprising:
a controller for moving the radiation source and the detector relative to the subject; and
a reconstruction processor for reconstructing an image from the corrected detection result,
wherein the controller rotates the radiation source and the detector relative to the subject, and
wherein the reconstruction processor performs a reconstructing operation by using the corrected detection result to acquire a three-dimensional image.

15. The radiation imaging apparatus according to claim 9, further comprising:
a collimator for adjusting an amount of radiation on the subject,
wherein the scattered X-ray radiation amount is changed by changing a width between shielding plates forming the collimator.

16. A radiation imaging apparatus, comprising:
a radiation source for irradiating a subject with radiation;
a detector having multiple pixels for detecting the radiation;
a storage means for storing a scattered radiation correction function for correcting influence of scattered radiation on a detection result obtained from the detector, and a beam hardening correction function for correcting influence of beam hardening on the corrected detection result;

a correction means for correcting the detection result by the scattered radiation correction function, and for correcting the corrected detection result by the beam hardening correction; and a correction function calculation means for calculating the beam hardening correction function from the detection result, wherein the correction function calculation means comprises:

a beam hardening function determination means for determining a beam hardening function for specifying an ideal value of the beam hardening amount in accordance with a transmission distance; and a beam hardening correction function generation means for calculating and plotting on a graph, the ideal value at an identical transmission distance by using the beam hardening function, with respect to each first projection data obtained by converting the transmittance data being obtained by minimizing the scattered radiation amount, approximating the values by an approximate curve, thereby determining the beam hardening correction function for returning projection data after the beam hardening correction, associated with the projection data calculated from the detection result.

17. The radiation imaging apparatus according to claim 16, further comprising;

a correction function calculation measuring means for performing correction function calculation measurement to obtain the first projection data by converting the transmittance data obtained by minimizing the scattered radiation amount at multiple transmission distances, wherein beam hardening function determination means plots on a graph the first projection data with respect to each transmission distance, approximates the data by a linear function passing through an original point, using the transmission distance as a variable, thereby determining the beam hardening function.

18. The radiation imaging apparatus according to claim 16, wherein the beam hardening correction function is calculated by using data measured with changes in a transmission distance, and returns a beam hardening correction value in response to the corrected detection result after correcting the influence of the scattered radiation.

19. The radiation imaging apparatus according to claim 16, further comprising:

a collimator for adjusting an amount of radiation on the subject, wherein the collimator is adjusted to have a collimator condition of a fan beam computed tomography (CT), so as to establish a state that the scattered radiation amount is nearly zero.

20. The radiation imaging apparatus according to claim 16, further comprising:

a correction function calculation means for calculating at least one of the scattered radiation correction function and the beam hardening correction function, respectively from the detection result.

* * * * *